United States Patent
Asano et al.

(10) Patent No.: US 9,731,083 B2
(45) Date of Patent: Aug. 15, 2017

(54) VALVED SYRINGE RECEPTACLE

(71) Applicant: DAIWA CAN COMPANY, Tokyo (JP)

(72) Inventors: Toshihiro Asano, Sagamihara (JP); Yoshiki Hamai, Tokyo (JP); Akira Nagashima, Tokyo (JP); Toshio Iino, Sagamihara (JP); Toshiaki Nakayama, Kitaadachi-gun (JP); Yuya Kawasaki, Mohka (JP); Makoto Takami, Sagamihara (JP)

(73) Assignee: Daiwa Can Company (JP)

( * ) Notice: Subject to any disclaimer, the term of this patent is extended or adjusted under 35 U.S.C. 154(b) by 0 days.

(21) Appl. No.: 15/142,417

(22) Filed: Apr. 29, 2016

(65) Prior Publication Data

US 2016/0243317 A1 Aug. 25, 2016

Related U.S. Application Data

(63) Continuation of application No. PCT/JP2014/079059, filed on Oct. 31, 2014.

(30) Foreign Application Priority Data

Oct. 31, 2013 (JP) .................................. 2013-227681
Apr. 10, 2014 (JP) .................................. 2014-081317

(51) Int. Cl.
*A61M 5/36* (2006.01)
*A61J 1/20* (2006.01)
*A61J 1/10* (2006.01)

(52) U.S. Cl.
CPC ............... *A61M 5/36* (2013.01); *A61J 1/201* (2015.05); *A61J 1/2096* (2013.01); *A61J 1/10* (2013.01)

(58) Field of Classification Search
CPC ... A61J 1/10; A61J 1/1406; A61J 1/1475; A61J 1/20; A61J 1/201; A61J 1/2037;
(Continued)

(56) References Cited

U.S. PATENT DOCUMENTS

| 4,066,079 A | 1/1978 | Chiarolla |
| 4,332,249 A | 6/1982 | Joslin |

(Continued)

FOREIGN PATENT DOCUMENTS

| EP | 0161797 A2 | 11/1985 |
| JP | S61-502170 A | 10/1986 |

(Continued)

OTHER PUBLICATIONS

Notification of Transmittal of Copies of Translation of International Preliminary Report on Patentability regarding International Application No. PCT/JP2014/079059 received on May 18, 2016 (5 pages).

(Continued)

*Primary Examiner* — Bryon Gehman
(74) *Attorney, Agent, or Firm* — Harness, Dickey & Pierce, P.L.C.

(57) ABSTRACT

A syringe receptacle includes a base portion including a communication hole formed such that an injection needle of a syringe is insertable; a container airtightly provided on the base portion; a space forming portion provided on the base portion and forming a space which is connected to the communication hole and an inside of the container; a first valve portion provided between the communication hole and the space, and configured to restrict a movement of a fluid from the space to the communication hole; and a second valve portion provided between the space and the inside of the container, and configured to restrict a movement from the inside of the container to the space.

4 Claims, 18 Drawing Sheets

(58) Field of Classification Search
CPC ...... A61J 1/2096; A61J 1/2062; A61J 1/2082;
A61J 1/2089; A61M 5/36; B32B 2439/46
USPC .................. 604/247, 408–412, 415, 416
See application file for complete search history.

(56) References Cited

U.S. PATENT DOCUMENTS

| | | | |
|---|---|---|---|
| 4,775,376 A | 10/1988 | Strung | |
| 4,838,875 A * | 6/1989 | Somor | A61M 39/26 604/247 |
| 5,006,118 A * | 4/1991 | Yule | A61J 1/067 604/408 |
| 5,147,309 A | 9/1992 | Hemmerich et al. | |
| 5,391,150 A * | 2/1995 | Richmond | A61J 1/10 604/247 |
| 6,695,829 B2 * | 2/2004 | Hellstrom | A61J 1/2096 604/415 |
| 6,773,427 B2 * | 8/2004 | Takagi | A61J 1/2089 604/408 |
| 8,973,622 B2 * | 3/2015 | Lopez | A61J 1/2096 141/27 |
| 9,345,643 B2 * | 5/2016 | Okiyama | A61J 1/2089 |
| 2006/0111667 A1 | 5/2006 | Matsuura et al. | |
| 2011/0224610 A1 | 9/2011 | Lum et al. | |
| 2015/0112296 A1 * | 4/2015 | Ishiwata | A61J 1/1406 604/415 |

FOREIGN PATENT DOCUMENTS

| | | |
|---|---|---|
| JP | S63-24955 A | 2/1988 |
| JP | 2002-331032 A | 11/2002 |
| JP | 2006-504455 A | 2/2006 |
| JP | 2007-275293 A | 10/2007 |

OTHER PUBLICATIONS

International Search Report (with English translation) regarding Application No. PCT/JP2014/079059 mailed Jan. 27, 2015 (6 pages).

Office Action issued by the Intellectual Property Office of Singapore (IPOS) mailed on Dec. 9, 2016 regarding corresponding Singapore Patent Application No. 11201603405Y (6 pages).

* cited by examiner

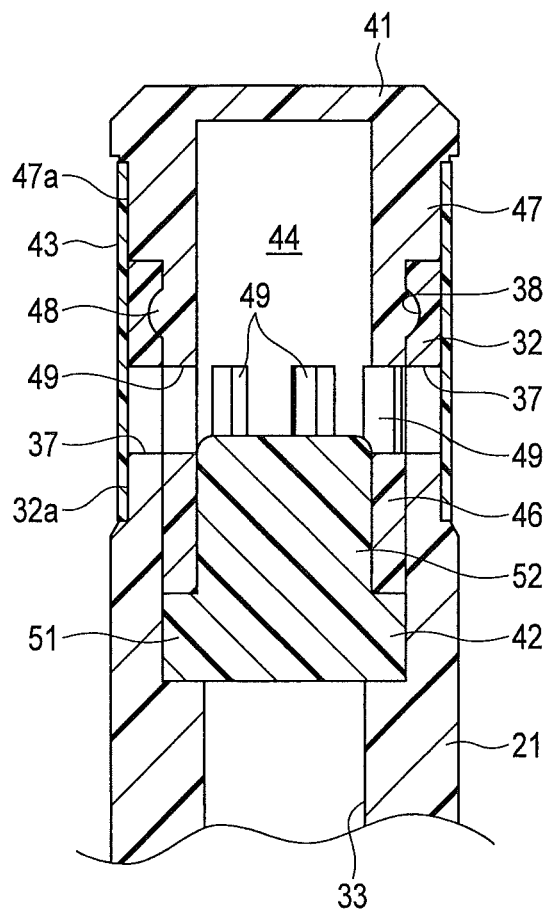
F I G. 3

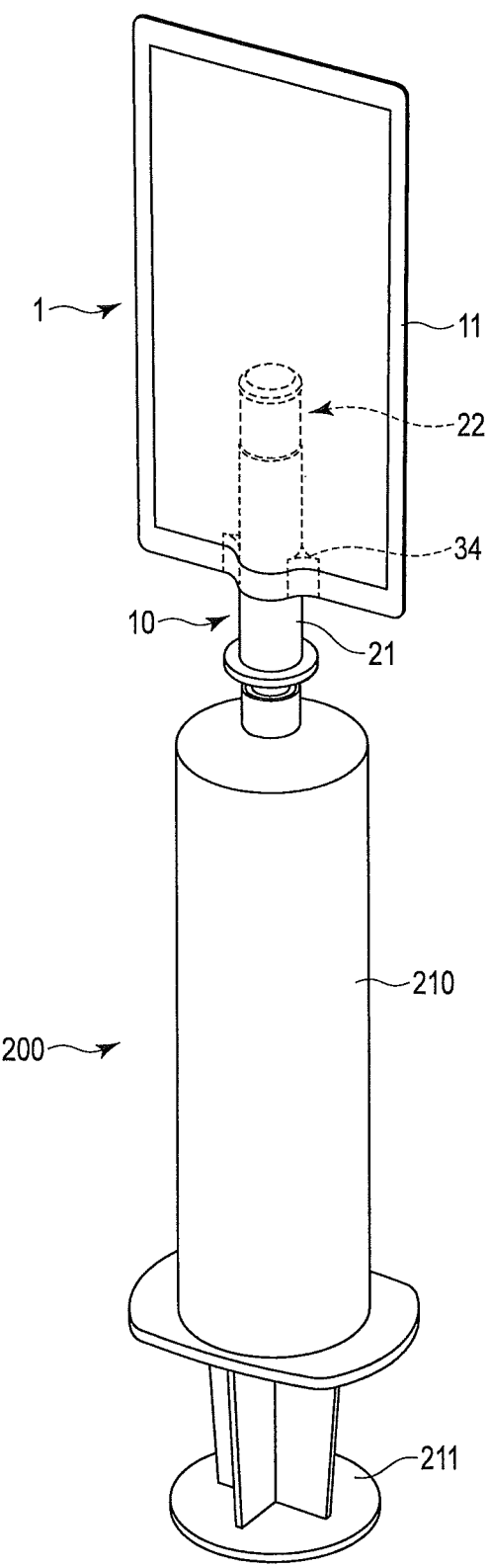
F I G. 4

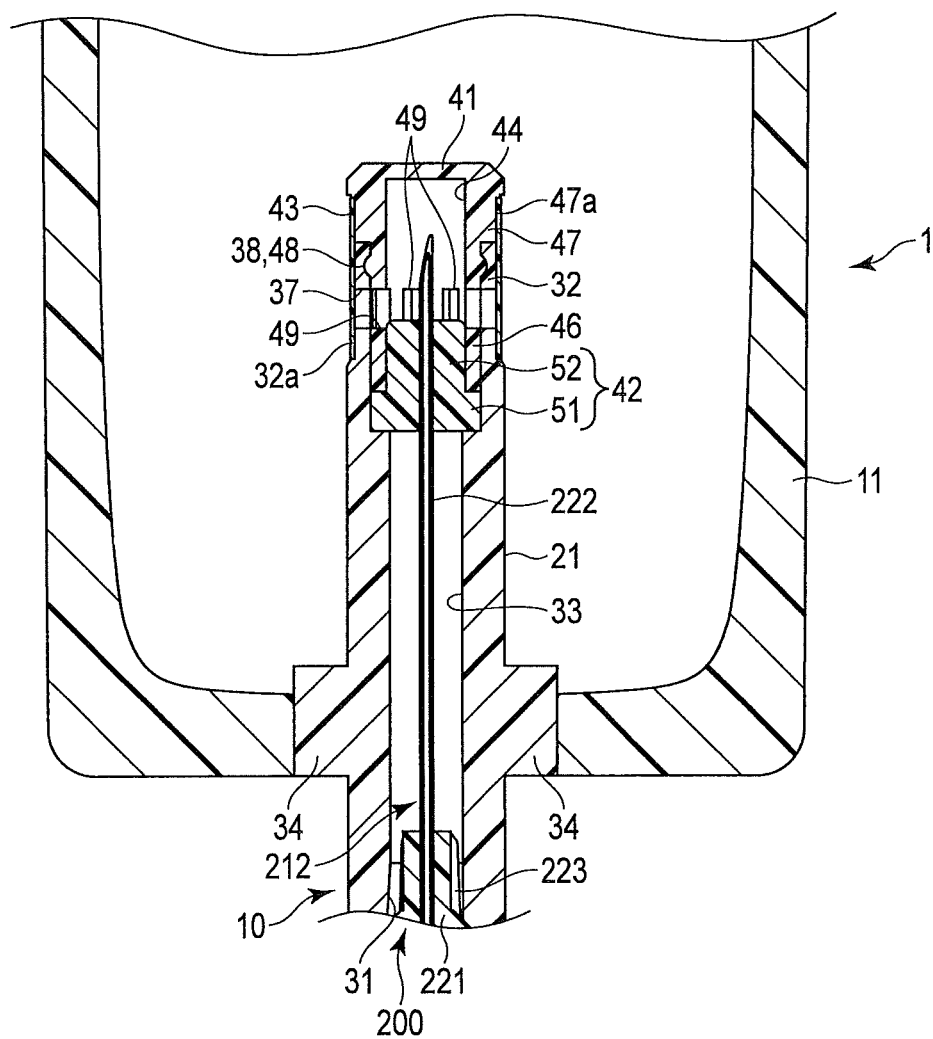
F I G. 5

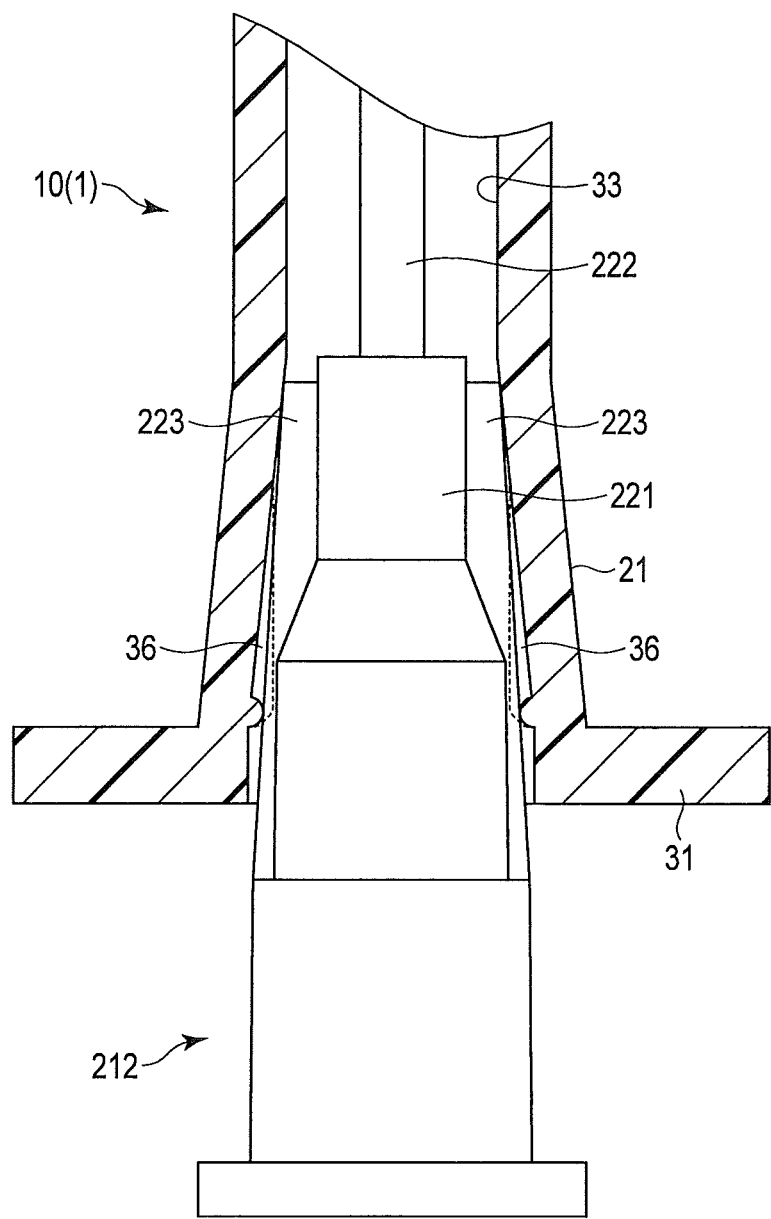
F I G. 6

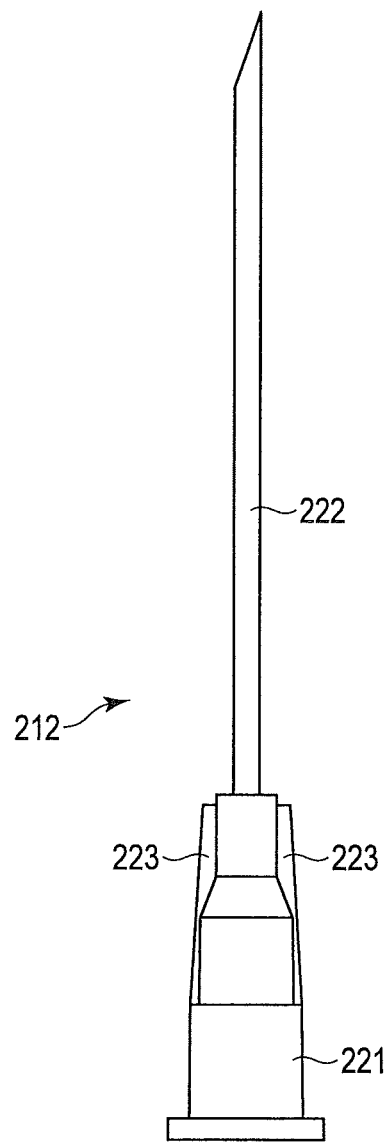
F I G. 8

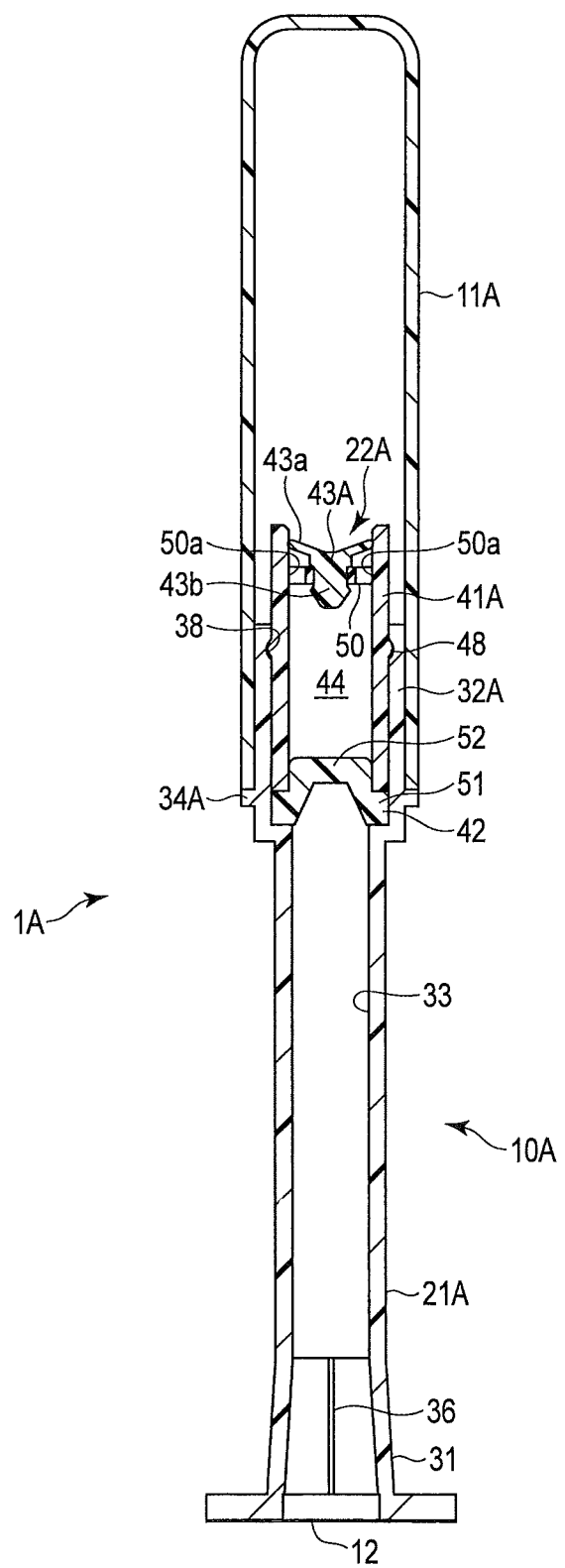
F I G. 9

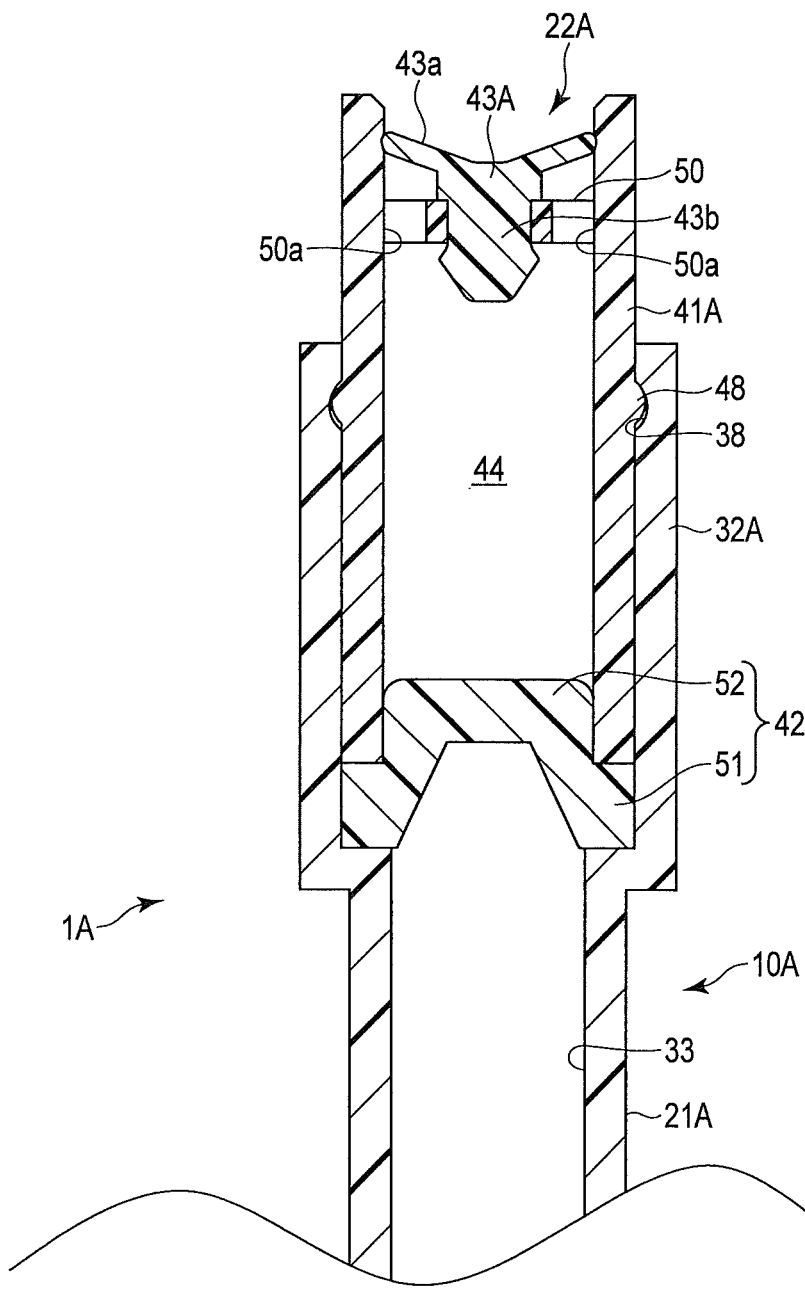
F I G. 10

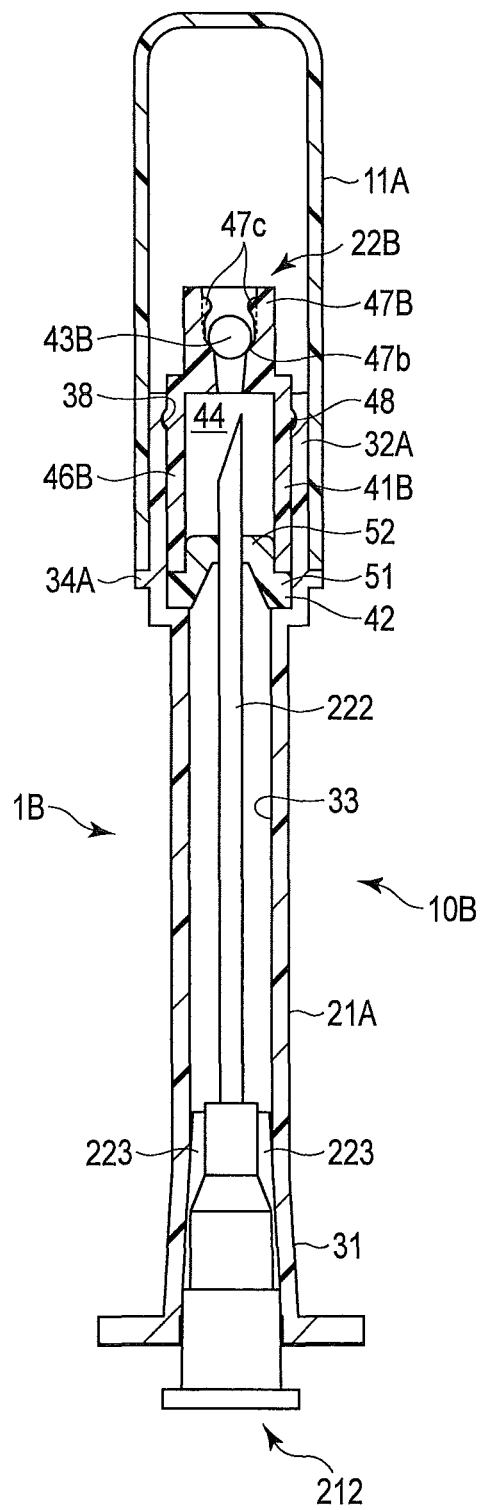
F I G. 12

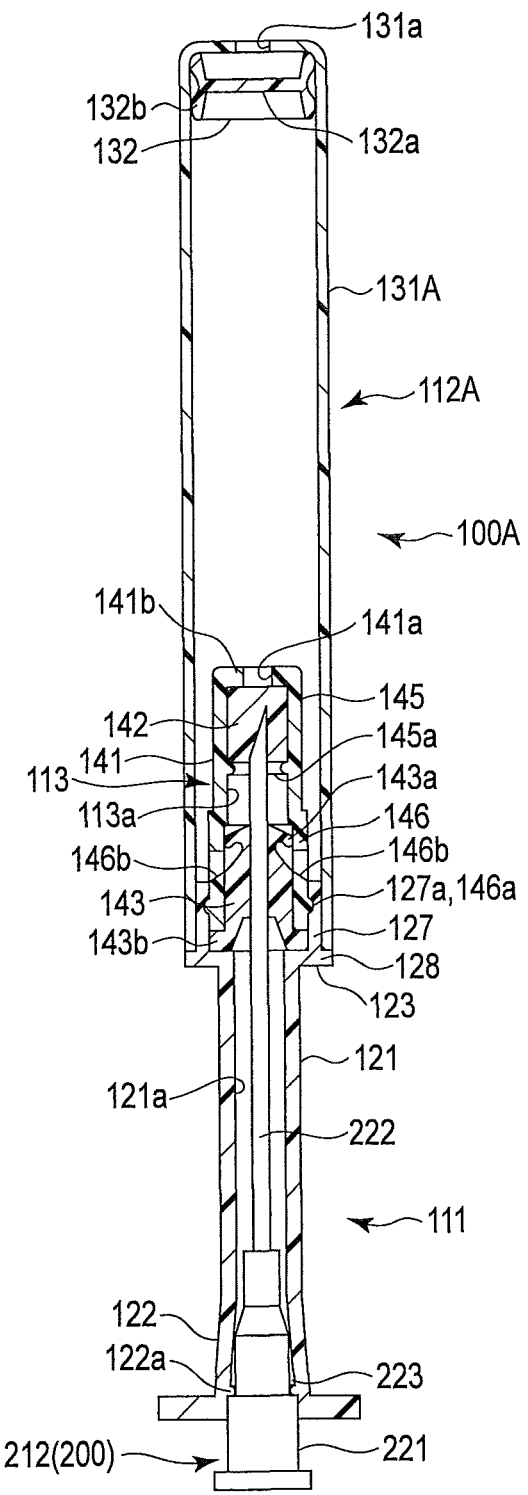
F I G. 16

VALVED SYRINGE RECEPTACLE

CROSS-REFERENCE TO RELATED APPLICATIONS

This is a Continuation Application of PCT application No. PCT/JP2014/079059, filed Oct. 31, 2014, which was published under PCT Article 21(2) in Japanese.

This application is based upon and claims the benefit of priority from Japanese Patent Application No. 2013-227681, filed Oct. 31, 2013, Japanese Patent Application No. 2014-081317, filed Apr. 10, 2014 the entire contents of all of which are incorporated herein by reference.

BACKGROUND OF THE INVENTION

1. Field of the Invention

The present invention relates to a syringe receptacle which contains an unnecessary medical fluid and gas which were sucked in a syringe.

2. Description of the Related Art

When a medical fluid is sucked from an ampoule into a syringe, a plunger is inserted into the barrel of the syringe down to a bottom dead point, and an injection needle is inserted into the ampoule. By moving the plunger up to a top dead point in this state, the medical fluid is sucked into a space formed by the barrel and plunger in the syringe. At this time, in some cases, air in the ampoule is also sucked.

In addition, when a medical fluid is drawn out of a vial into a syringe, an amount of air, which is slightly less than the volume of the medical fluid that is to be drawn out of the vial, is first sucked into the syringe, and then the injection needle is pierced into an elastic cap of the vial.

Subsequently, the plunger of the syringe is reciprocally moved, and the air in the syringe is replaced with the medical fluid in the vial. At this time, in order to prevent the pressure in the vial from becoming a positive pressure, and to prevent the medical fluid in the vial from leaking, the plunger of the syringe is reciprocally moved a plurality of times, so as to keep the pressure in the vial in a range between a weak negative pressure and an equilibrium pressure. In addition, when the injection needle is pulled out of the vial, the air in the vial is sucked into the syringe in order to set the pressure in the vial at a negative pressure and to remove the medical fluid remaining in the injection needle.

In order to remove the air sucked in the syringe and to set the amount of the medical fluid in the syringe at a desired amount, the injection needle is turned upward, the air is positioned upward in the space in the syringe, and the plunger is pushed to the bottom dead point. Thereby, a work of removing the air and excess medical fluid from the syringe is performed.

When such a work of removing the air and excess medical fluid from the syringe is performed, there is concern that air, a gas including a medical fluid, or a small amount of medical fluid is discharged from the syringe, and adheres to the worker or flies to the surrounding. This becomes a cause of contamination in the surrounding. Further, if the medical fluid is toxic, there is concern that the worker's health is endangered.

This being the case, Jpn. Pat. Appln. KOKAI Publication No. 2007-275293 discloses an air removing apparatus which can prevent contamination of the surrounding and can take air out of a syringe in a work of removing air. This air removing apparatus includes a space portion for storing a medical fluid in a container, and a filter portion which can pass the air in the space portion. This air removing apparatus captures a medical fluid included in the air by the filter portion. In addition, in this air removing apparatus, a communication tube, which connects the space portion and the filter portion, is projected from the inner surface of the space portion. Thereby, it is possible to prevent a medical fluid from moving to the outside, for example, even when the container is inclined. Thus, even if a work of removing air in the syringe, contamination in the surrounding due to a medical fluid can be prevented.

BRIEF SUMMARY OF THE INVENTION

As an aspect of the present invention, a syringe receptacle includes a base portion including a communication hole formed such that an injection needle of a syringe is insertable; a container airtightly provided on the base portion; a space forming portion provided on the base portion and forming a space which is connected to the communication hole and an inside of the container; a first valve portion provided between the communication hole and the space, and configured to restrict a movement of a fluid from the space to the communication hole; and a second valve portion provided between the space and the inside of the container, and configured to restrict a movement from the inside of the container to the space.

BRIEF DESCRIPTION OF THE SEVERAL VIEWS OF THE DRAWING

FIG. 3 is a cross-sectional view illustrating the structure of a main part of the syringe receptacle.

FIG. 4 is a perspective view illustrating an example of use of the syringe receptacle.

FIG. 5 is a cross-sectional view illustrating an example of use of the structure of the main part of the syringe receptacle.

FIG. 6 is a partially cross-sectional side view illustrating an example of use of the structure of the main part of the syringe receptacle.

FIG. 8 is a side view illustrating the structure of an injection needle of a syringe which is used for the syringe receptacle.

FIG. 9 is a cross-sectional view illustrating the structure of a syringe receptacle according to a second embodiment of the present invention.

FIG. 10 is a cross-sectional view illustrating the structure of a main part of the syringe receptacle.

FIG. 12 is a cross-sectional view illustrating the structure of a syringe receptacle according to a third embodiment of the present invention.

FIG. 16 is a cross-sectional view illustrating the structure of a syringe receptacle according to a fifth embodiment of the present invention.

DETAILED DESCRIPTION OF THE INVENTION

First Embodiment

Hereinafter, the structure of a syringe receptacle 1 according to a first embodiment of the present invention will be described with reference to FIG. 1 to FIG. 8.

Figure 1:
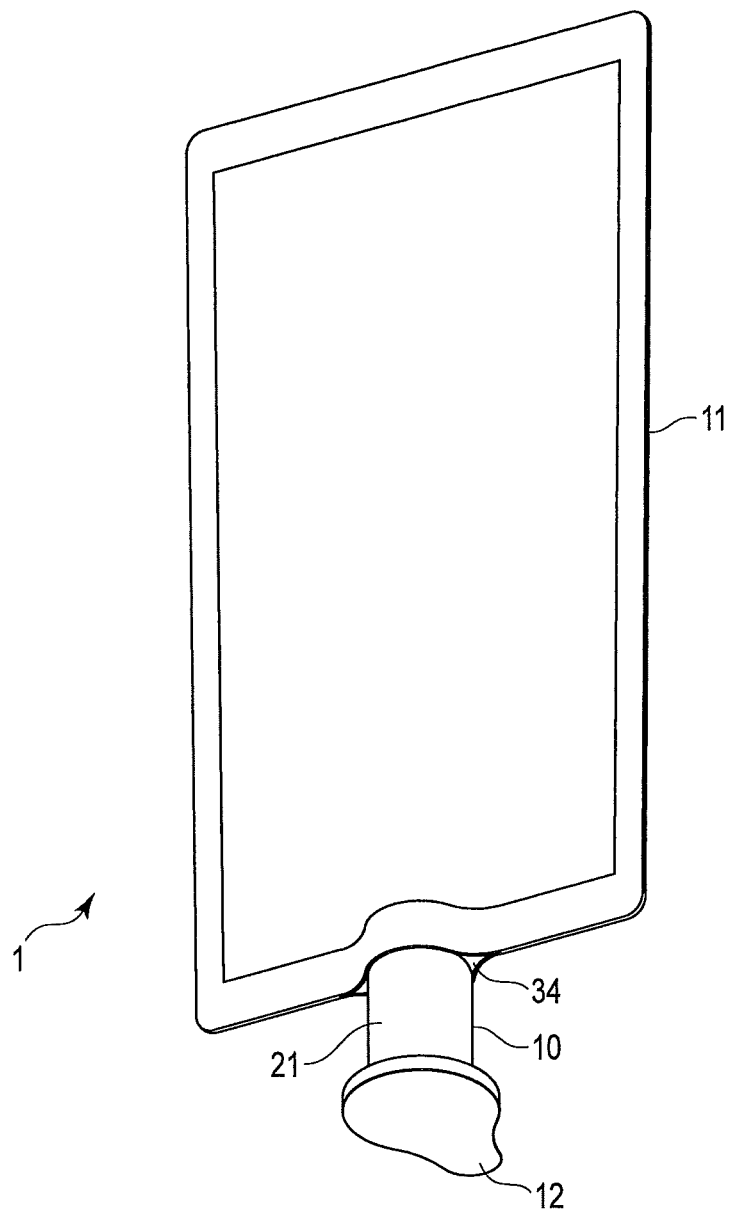
FIG. 1 is a perspective view illustrating the structure of a syringe receptacle according to a first embodiment of the present invention.
Figure 2:
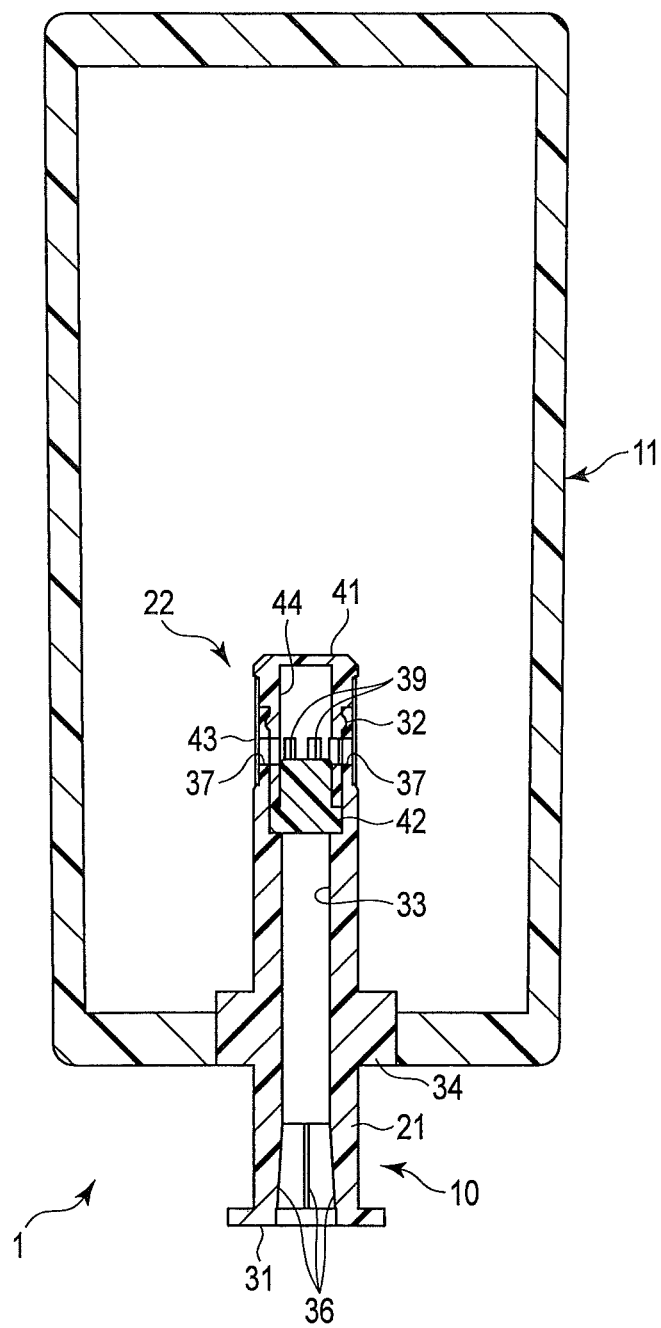
FIG. 2 is a cross-sectional view illustrating the structure of the syringe receptacle.
Figure 7:
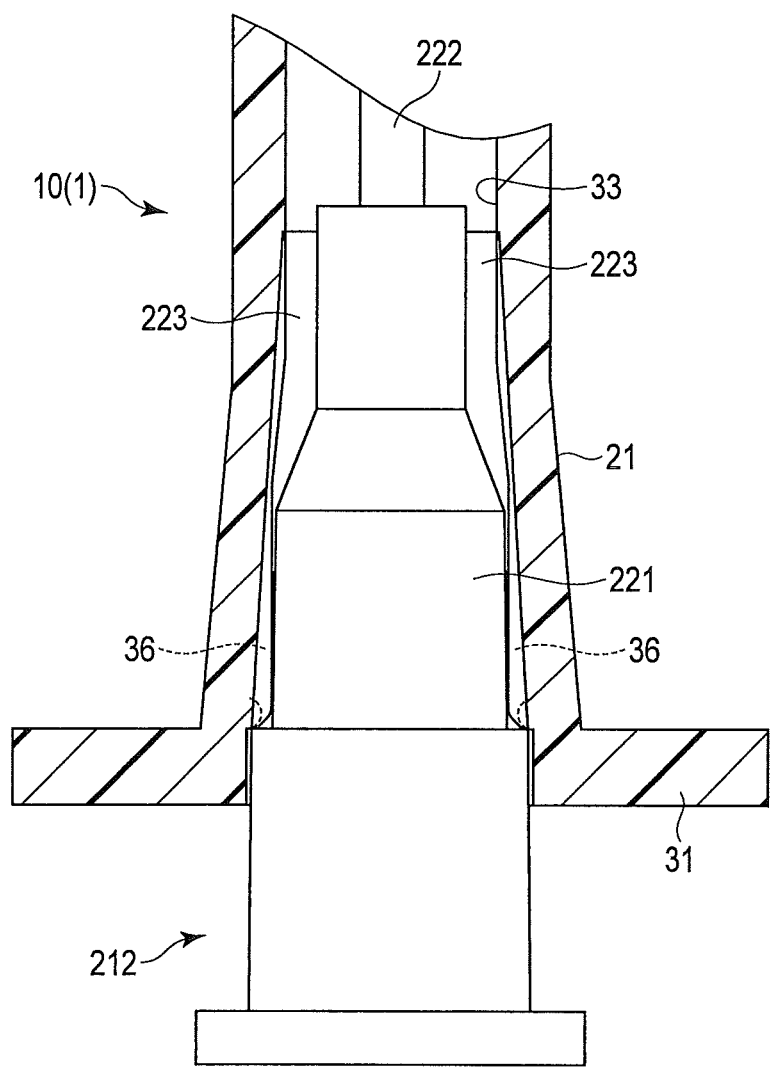
FIG. 7 is a partially cross-sectional side view illustrating an example of use of the structure of the main part of the syringe receptacle.

FIG. 1 is a perspective view illustrating the structure of the syringe receptacle 1 according to the first embodiment of the present invention. FIG. 2 is a cross-sectional view illustrating the structure of the syringe receptacle 1. FIG. 3 is a cross-sectional view illustrating the structure of a main part of the syringe receptacle 1, to be more specific, the structure of a spout portion 10. FIG. 4 is a perspective view illustrating an example of use of the syringe receptacle 1, to be more specific, an air removing work of a syringe 200. FIG. 5 is a cross-sectional view illustrating the structure of the spout portion 10 in the air removing work of the syringe 200 of the syringe receptacle 1. FIG. 6 is a partially cross-sectional side view illustrating an example at a time when an injection needle 212 is inserted in the spout portion 10. FIG. 7 is a partially cross-sectional side view illustrating an example at a time when the injection needle 212 is inserted in the spout portion 10. FIG. 8 is a side view illustrating the structure of the injection needle 212 which is used for the syringe 200.

The syringe receptacle 1 is used for storing air, air (gas) including a medical fluid, or part of a medical fluid, when the medical fluid was sucked in a syringe 200 and air included in the medical fluid is pushed out of the syringe 200.

In the meantime, as illustrated in FIG. 4 to FIG. 8, the syringe 200, which is used for the syringe receptacle 1, includes a barrel 210 which is formed in a cylindrical shape and has one end with a reduced diameter; a plunger 211 which is inserted in the barrel 210; and an injection needle 212 provided on the distal end of the barrel 210, which has the reduced diameter.

The plunger 211 is a piston which is reciprocally movable in the barrel 210. The plunger 211 and the barrel 210 form, within the syringe 200, a space which can store a medical fluid. The injection needle 212 is detachably provided on the barrel 210. As illustrated in FIG. 5 to FIG. 8, the injection needle 212 is formed of a metallic material or a resin material, and includes a coupling portion 221 which is fixed to the barrel 210, and a needle portion 222 provided on the coupling portion 221.

The coupling portion 221 is formed in a cylindrical shape having a plurality of different outside diameters and a reduced inside diameter, and is formed to be engageable with the distal end of the barrel 210, which has the reduced diameter. In addition, the needle portion 222 is put in close contact with, and fixed to, the inner peripheral surface of the coupling portion 221. The coupling portion 221 includes, for example, on a part of the outer peripheral surface thereof, a plurality of projection portions 223 which are provided to extend along the the longitudinal direction of the coupling portion 221 and which have outer surfaces that are inclined relative to the axis of the coupling portion 221.

The plural projection portions 223 are disposed, for example, at equal intervals at four locations on the outer peripheral surface of the coupling portion 221. The needle portion 222 is formed in such a cylindrical shape that a fluid can move therein, and a distal end of the needle portion 222 is formed at such an acute angle as to be capable of piercing.

As illustrated in FIG. 1 to FIG. 3, the syringe receptacle 1 includes a spout portion 10, a container 11 and a cover portion 12. The syringe receptacle 1 has a so-called spout-pouch form, in which a pouch with flexibility, for instance, is used as the container 11.

The spout portion 10 includes a base portion 21 which is formed in a cylindrical shape, and a valve portion 22 which is provided at an end portion of the base portion 21. The base portion 21 has one end opened and exposed to the outside of the container 11, and has the other end disposed within the container 11. In addition, the base portion 21 is provided with the valve portion 22 at the other end portion.

Specifically, the base portion 21 includes a first opening portion 31 provided at one end portion thereof, a second opening portion 32 provided at the other end portion, and a communication hole 33 which makes the first opening portion 31 and second opening portion 32 communicate with each other. In addition, the base portion 21 includes, on the outside thereof, an attachment portion 34 for attachment of the container 11.

The first opening portion 31 constitutes one end portion of the base portion 21. The first opening portion 31 is formed to have an inside diameter which gradually decreases from the one end portion to the other end portion of the base portion 21, or in other words, toward the second opening portion 32. Specifically, the first opening portion 31 opens in a truncated conical shape. The angle of inclination and the inside diameter of the first opening portion 31 are formed to be substantially identical to the angle of inclination of the outer surface of the projection portions 233 provided on the coupling portion 221 of the injection needle 212, and to the width between a pair of projection portions 223 which are opposed to each other. In addition, the first opening portion 31 includes, on the inner peripheral surface thereof, a plurality of projection portions 36 which are provided along the direction of inclination of the inner peripheral surface.

The projection portions 36 are provided at equal intervals on the inner peripheral surface of the first opening portion 31. The projection portions 36 are formed such that the side surfaces thereof can abut on the side surfaces of the projection portions 223 provided on the coupling portion 221. In other words, the projection portions 36 are formed to be capable of interfering, in the circumferential direction, with the projection portions 223 provided on the coupling portion 221.

The second opening portion 32 constitutes the other end portion of the base portion 21. The second opening portion 32 is formed such that the inner peripheral surface thereof is greater in diameter than the inner peripheral surface of the communication hole 33. A plurality of openings 37 are formed in a part of the second opening portion 32 at equal intervals along the circumferential direction.

In the second opening portion 32, an annular recess portion 38 is formed in a part of the inner peripheral surface thereof, for example, in an inner peripheral surface on the end portion side of the plural openings 37. The recess portion 38 is formed to have, for example, a semicircular cross-sectional shape. In addition, an outer peripheral surface 32a of the second opening portion 32 is formed to have an outside diameter which is slightly less than the outside diameter of the other part of the base portion 21.

The communication hole 33 is formed with a uniform diameter. The communication hole 33 is formed to be shorter than the length of the needle portion 222 which projects from the coupling portion 221 of the injection needle 212.

The attachment portion 34 is formed to be capable of airtightly fixing the container 11. For example, the attachment portion 34 is fusion-bonded to the container 11, and thus the attachment portion 34 is formed to be fixable to the container 11.

The valve portion 22 includes a stationary portion 41 which is fixed to the second opening portion 32; a first valve portion 42; and a second valve portion 43. The valve portion 22 is a check valve which is provided at the end portion of the base portion 21. In addition, the valve portion 22 forms a space 44 which is sealed between the communication hole 33 and container 11 and communicates with the communication hole 33 and container 11.

The stationary portion 41 is formed in a cup shape with one end closed, and an opening end portion of the stationary portion 41 is fixed to the second opening portion 32. For example, the stationary portion 41 is formed to have a plurality of different outside diameters. Specifically, the stationary portion 41 includes a first stationary portion 46 which is formed on the opening end side of the stationary portion 41 and has an outside diameter that is equal to the inside diameter of the second opening portion 32; and a second stationary portion 47 which is formed on the closed end side of the stationary portion 41 and has an outside diameter of a part neighboring the first stationary portion 46, which is equal to the outside diameter of the second opening portion 32. The stationary portion 41 is a space forming portion which forms, together with the valve portion 42, the space 44 in the inside thereof.

In a part of the first stationary portion 46, a plurality of openings 49 are formed at equal intervals along the circumferential direction. The openings 49 are formed such that when the stationary portion 41 is fixed to the second opening portion 32, the openings 49 can be opposed to, and can communicate with, at least a part of the openings 37 of the second opening portion 32.

In the first stationary portion 46, an annular projection portion 48 is formed on a part of the outer peripheral surface thereof, for example, on the closed end side of the plural openings 49, or in other words, on the outer peripheral surface on the second stationary portion 47 side. The projection portion 48 is formed to have, for example, a semicircular cross-sectional shape. The projection portion 48 is formed to be engageable with the recess portion 38 of the second opening portion 32 when the stationary portion 41 is fixed to the second opening portion 32. In addition, the first stationary portion 46 is formed to have a length in the axial length, which is less than the length from the end portion of the second opening portion 32 to the communication hole 33.

The second stationary portion 47 is formed such that the outside diameter thereof on the closed end side of the stationary portion 41 is equal to the outside diameter of the second opening portion 32 which neighbors the first stationary portion 46. An outer peripheral surface 47a of the second stationary portion 47, together with the outer peripheral surface 32a of the second opening portion 32, forms an annular groove portion which is formed such that the second valve portion 43 can be fixed.

The first valve portion 42 is formed of an elastically deformable resin material, and is formed in a columnar shape with different outside diameters. The first valve portion 42 is a so-called rubber stopper, which is a stopper formed of an elastic body. The elastic body is formed to be pierceable by the injection needle 212, and to be capable of closing, after the injection needle 212 was pierced, a hole formed by the piercing.

The first valve portion 42 includes a disc-shaped first portion 51 which is formed to have an outside diameter that is substantially equal to or slightly greater than the inside diameter of the second opening portion 32; and a columnar second portion 52 which is formed to have an outside diameter that is substantially equal to or slightly greater than the inside diameter of the first stationary portion 46.

The first portion 51 is formed such that the length thereof in the axial direction is slightly greater than a difference between the length from the end portion of the second opening portion 32 to the communication hole 33 and the length of the first stationary portion 46. The first portion 51 lies between the second opening portion 32 and the first stationary portion 46, and thereby the first portion 51 is clamped by the second opening portion 32 and the first stationary portion 46 and airtightly fixed.

The second portion 52 is formed such that the length thereof in the axial direction is substantially equal to the length from the end portion of the first stationary portion 46 to the openings 49. The second portion 52 forms the space 44 in the inside of the stationary portion 41 by the end face of the second portion 52 and the inner surface of the stationary portion 41.

The second valve portion 43 is formed of a resin material with flexibility, or the like, in a cylindrical shape. To be more specific, the second valve portion 43 is formed in a tubular shape, and is formed such that the inside diameter thereof is slightly less than the outside diameters of the outer peripheral surfaces 32a and 47a of the second opening portion 32 and second stationary portion 47.

The second valve portion 43 is disposed in the groove portion which is formed by the outer peripheral surfaces 32a and 47a of the second opening portion 32 and second stationary portion 47, and thereby the inner peripheral surface of the second valve portion 43 is put in close contact with the outer peripheral surfaces 32a and 47a. With the second valve portion 43 being provided in the groove portion, the second valve portion 43 is formed to be capable of sealing, by the inner peripheral surface thereof, the openings 37 and 49 and the gap between the second opening portion 32 and second stationary portion 47.

The container 11 is a so-called pouch, which is formed by attaching films which are formed of a resin material with flexibility. A peripheral part of the container 11 is adhered, and the container 11 is airtightly fixed to the base portion 21, and thereby the container 11 is formed with the inside thereof sealed.

The cover portion 12 is formed to be capable of closing the first opening portion 31 of the base portion 21. By being adhered to the end face of the first opening portion 31, the cover portion 12 closes the opening of the first opening portion 31. After adhering the cover portion 12 and closing the first opening portion 31, the entirety of the container is sterilized by, for example, radiation sterilization. Thereby, until the cover portion 12 is peeled off, the cover portion 12 can keep the inside of the container 11 in a sterile state.

Next, a method of use of the syringe receptacle 1 with the above-described structure is described.

To begin with, a medical fluid is filled in the syringe 200. Specifically, when a medical fluid is sucked from an ampoule into the syringe 200, a worker inserts the plunger 211 into the barrel 210 of the syringe 200 down to the bottom dead point, and inserts the injection needle into the ampoule. In this state, the plunger 211 is moved up to the top dead point. Thereby, the medical fluid is sucked into the space which is formed within the syringe 200 by the barrel 210 and plunger 211. In the suction of the medical fluid, if air is also sucked in the syringe 200, the cover portion 12 is first removed from the first opening portion 31.

Next, as illustrated in FIG. 6, the injection needle 212 is inserted into the spout portion 10 until the projection portions 223 of the coupling portion 221 abut on the inner peripheral surface of the first opening portion 31 of the spout portion 10. Thereby, the injection needle 212 passes through the communication hole 33, and pierces into the first valve portion 42. At this time, the distal end of the needle portion 222 penetrates the first valve portion 42, and is located in the space 44.

Subsequently, the syringe receptacle 1 and syringe 200 are inclined such that the injection needle 212 is positioned upward. Specifically, the syringe receptacle 1 and syringe 200 are disposed such that the syringe 200 moves downward in the direction of gravity of the syringe receptacle 1. Thereby, the air in the syringe 200 moves to the injection needle 212 side.

Next, the worker pushes the plunger 211 into the barrel 210, and discharges the air in the syringe 200 from the injection needle 212. Thereby, air, air (gas) including a medical fluid, or part (e.g. air) of a medical fluid is discharged into the space 44. If the air or the like moves into the space 44, the pressure in the space 44 increases. By the increase in pressure, the second valve portion 43 is pushed via the openings 37 and 49, the second valve portion 43 is spaced apart from the outer peripheral surface 32a and 47a, and the space 44 and the inside of the container 11 communicate with each other. The air or the like in the space 44 moves into the container 11 until the pressure in the space 44 becomes equal to the pressure in the container 11. If the air or the like in the space 44 moves into the container 11, the second valve portion 43 seals the openings 37 and 49 by the restoring force thereof, and the space 44 and the inside of the container 11 are shut off from each other.

Then, the worker removes the syringe 200 from the syringe receptacle 1. Thereby, the first valve portion 42 closes, by the restoring force thereof, the hole that was formed by the piercing of the injection needle 212, and the space 44 is shut off from the communication hole 33. Thus, the air removing work of the syringe 200 is completed.

According to the syringe receptacle 1 with the above-described structure, by the air removing work of the syringe 200, the air in the syringe 200 can be discharged into the container 11, and the air can be removed from the inside of the syringe 200. In addition, even if a medical fluid is included in the discharged air or even if a medical fluid is discharged together with the air when the air is discharged, the medical fluid moves from the space 44 into the container 11 and can be discharged into the container 11. Furthermore, even if part of the air or the like, which was discharged to the space 44, does not move into the container 11 and stays in the space 44, the air or the like does not leak to the outside, since the first valve portion 42 shuts off the space 44 and the communication hole 33 from each other.

In this manner, the syringe receptacle 1 can safely and exactly discharge the air, which was sucked in the syringe 200 together with the medical fluid, from the syringe 200, without leaking the discharged air or the like. It is thus possible to prevent the influence on the worker or the contamination in the surrounding due to the leak, etc. of the medical fluid.

In the syringe receptacle 1, the space 44 and the communication hole 33 are shut off from each other by using, as the first valve portion 42, the stopper that is formed of an elastic body. Thus, there is no need to additionally close the hole that was formed by the piercing of the needle portion 222. Therefore, the syringe receptacle 1 is good in work efficiency.

In addition, when it is possible to remove the injection needle 212 from the syringe 200 after removing air in the syringe 200, and to discard the injection needle 212, the syringe receptacle 1 and the injection needle 212 can be discarded as one piece. If a concrete description is given, as illustrated in FIG. 7, the injection needle 212 is further inserted into the first opening portion 31. By this insertion, the projection portions 223 are elastically deformed. Thereafter, the syringe 200 is rotated, and thereby the projection portions 223 of the coupling portion 221 and the projection portions 36 of the first opening portion 31 are engaged and the movement in the rotational direction of the coupling portion 221 is restricted. At this time, the needle portion 222 is held by a predetermined holding force by the restoring force of the first valve portion 42, and, furthermore, the projection portions 223 are engaged in the first opening portion 31. As a result, although the barrel 210 and the coupling portion 221 are disengaged, the injection needle 212 remains in the state in which the injection needle 212 is fixed in the first valve portion 42, and the injection needle 212 is fixed to the syringe receptacle 1 as one piece. Thus, the injection needle 212 together with the syringe receptacle 1 can be discarded.

In the meantime, in the state in this case, the space 44 communicates with the outside via the hole of the needle portion 222. However, since the space 44 and the inside of the container 11 are shut off from each other by the second valve portion 43, the pressure in the container 11 does not act in the space 44, and the gas and medical fluid in the space 44 do not leak to the outside.

In addition, in this case, the shape of the first opening portion 32 may be set such that the coupling portion 221 is accommodated in the first opening portion 32. By this setting of the shape, in the state in which the removed injection needle 212 is disposed in the base portion 21, the first opening portion 32 can be closed by the cover portion 12 or a cap (not shown). Thereby, even when the syringe receptacle 1 including the injection needle 212 is discarded, it is possible to prevent the injection needle 212 from being exposed to the outside. Furthermore, when the toxicity of the medical fluid is high and the exposure of the medical fluid in the space 44 and injection needle 212 to the outside is not permitted at all, it is possible to attach the syringe 200 to the syringe receptacle 1 once again after the medical fluid in the syringe 200 was used. Thereby, the syringe 200 and the syringe receptacle 1 can be safely discarded together.

Moreover, the syringe receptacle 1 may be simply configured such that the first valve portion 42 and second valve portion 43, which are elastically deformable, are provided on a primary side and a secondary side of the space 44. Thus, the manufacturing cost of the syringe receptacle 1 can be reduced. In particular, since the syringe receptacle 1 is discarded after use, the running cost in the case of use in medical practice, etc. can be reduced.

Besides, the air, etc. discharged from the syringe 200 is contained in the container 11, and the inside of the container 11 is shut off from the outside by the two valve portions 42 and 43. Therefore, high safety can be ensured.

As described above, according to the syringe receptacle 1 of the first embodiment of the present invention, a fluid such as air, which is discharged from the syringe 200, can be safely contained in the container 11, and the manufacturing cost can be reduced.

Second Embodiment

Next, the structure of a syringe receptacle 1A according to a second embodiment of the present invention will be described with reference to FIG. 9 to FIG. 11.

FIG. 9 is a cross-sectional view illustrating the structure of the syringe receptacle 1A according to the second embodiment of the invention. FIG. 10 is a cross-sectional view illustrating the structure of the syringe receptacle 1A. FIG. 11 is a cross-sectional view illustrating the structure of a main part of the syringe receptacle 1A, to be more specific, the structure of a valve portion 22A which is used in a spout portion 10A. Of the structure of the syringe receptacle 1A according the second embodiment, the same structural parts as the structural parts of the syringe receptacle 1 according to the above-described first embodiment are denoted by like reference numerals, and a detailed description thereof is omitted.

Like the above-described syringe receptacle 1, the syringe receptacle 1A is used for storing air or the like, when a medical fluid was sucked in the syringe 200 and air included in the medical fluid is pushed out of the syringe 200.

Figure 11:
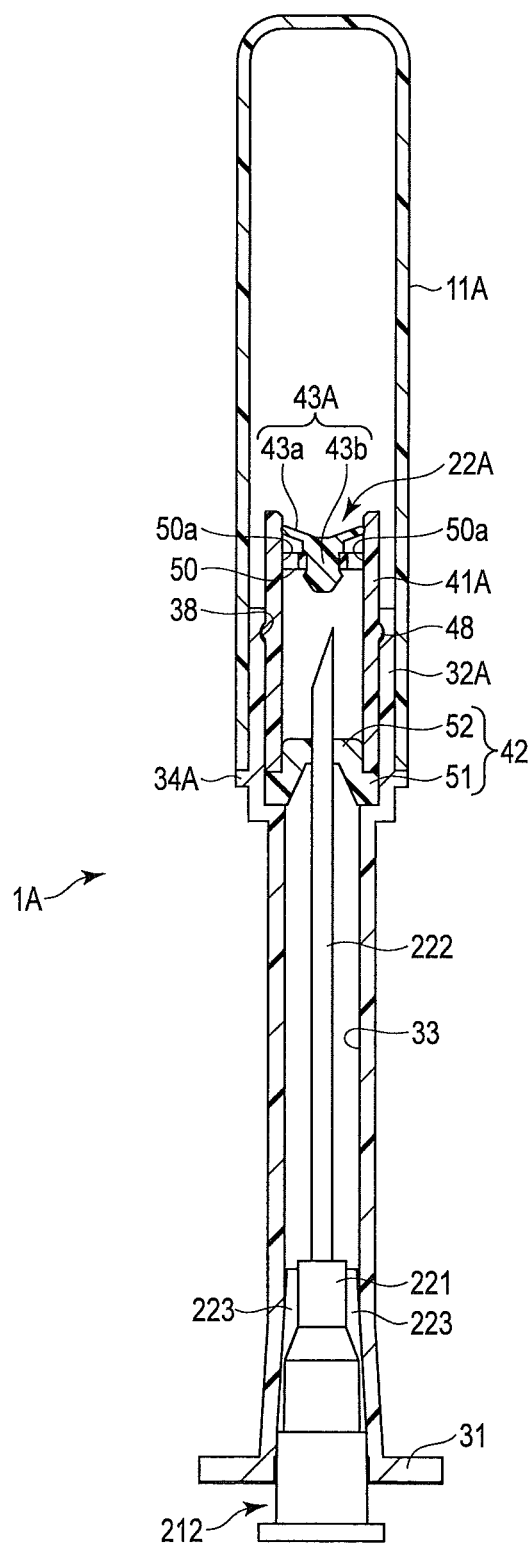
FIG. 11 is a cross-sectional view illustrating an example of use of the syringe receptacle.

As illustrated in FIG. 9 to FIG. 11, the syringe receptacle 1A includes a spout portion 10A, a container 11A and a cover portion 12.

The spout portion 10A includes a base portion 21A which is formed in a cylindrical shape, and a valve portion 22A which is provided at an end portion of the base portion 21A. The base portion 21A has one end opened and exposed to the outside of the container 11A, and has the other end disposed within the container 11A. In addition, the base portion 21A is provided with the valve portion 22A at the other end portion.

Specifically, the base portion 21A includes a first opening portion 31 provided at one end portion thereof, a second opening portion 32A provided at the other end portion, and a communication hole 33 which makes the first opening portion 31 and second opening portion 32A communicate with each other. In addition, the base portion 21A includes, on the outside thereof, an attachment portion 34A for attachment of the container 11A.

The second opening portion 32A constitutes the other end portion of the base portion 21A. The second opening portion 32A is formed such that the inner peripheral surface thereof is greater in diameter than the inner peripheral surface of the communication hole 33. An annular recess portion 38 is formed in a part of the inner peripheral surface of the second opening portion 32A.

The attachment portion 34A is formed such that the container 11A can be airtightly fixed. For example, the attachment portion 34A is a flange which is formed of an annular projection. The container 11A is adhered or fusion-bonded to the attachment portion 34A, thereby fixing the spout portion 10A and container 11A.

The valve portion 22A includes a stationary portion 41A which is fixed to the second opening portion 32A; a first valve portion 42; and a second valve portion 43A. The valve portion 22A is a check valve which is provided at the end portion of the base portion 21A. In addition, the valve portion 22A forms a space 44 which is sealed between the communication hole 33 and container 11A and communicates with the communication hole 33 and container 11A.

The stationary portion 41A is formed in a cylindrical shape with both ends opened, the stationary portion 41A having an outside diameter which is equal to the inside diameter of the second opening portion 32A. In the stationary portion 41A, a projection portion 48 is formed on a part of the outer peripheral surface thereof. By being inserted in the second opening portion 32A, the stationary portion 41A is fixed. In addition, the stationary portion 41A includes, on the inner peripheral surface thereof, an annular supporting portion 50, in a part of which a plurality of openings 50a are formed.

The supporting portion 50 is formed such that the second valve portion 43A can be fixed in a central opening of the supporting portion 50. In addition, the supporting portion 50 is formed to be capable of permitting communication between the space 44 and container 11A via the openings 50a.

The first valve portion 42 is formed of an elastically deformable resin material, and is formed in a columnar shape with different outside diameters. As illustrated in FIG. 9 to FIG. 11, for example, the first valve portion 42 may be configured such that a part of one of end faces thereof is notched. The first valve portion 42 is a so-called rubber stopper, which is a stopper formed of an elastic body. The elastic body is formed to be pierceable by the injection needle 212, and to be capable of closing, after the injection needle 212 was pierced, a hole formed by the piercing.

The first valve portion 42 includes a disc-shaped first portion 51 which is formed to have an outside diameter that is substantially equal to or slightly greater than the inside diameter of the second opening portion 32A; and a columnar second portion 52 which is formed to have an outside diameter that is substantially equal to or slightly greater than the inside diameter of the stationary portion 41A.

The first portion 51 is clamped between the second opening portion 32A and stationary portion 41A, and thereby the first portion 51 is fixed and makes sealing between the second opening portion 32A and stationary portion 41A.

The second valve portion 43A includes a disc-shaped valve body 43a, and a columnar supported portion 43b which is provided at the center of the valve body 43a. In the second valve portion 43A, the valve body 43a is formed of a resin material or the like so as to be deformable, and the valve body 43a and the supported portion 43b are formed as one piece.

The valve body 43a is formed to have an outside diameter which is slightly larger than the inside diameter of the stationary portion 41A. The supported portion 43b is engaged with the central opening of the supporting portion 50, and thereby the supported portion 43b is supported by the supporting portion 50. In this second valve portion 43A, the supported portion 43b is supported by the supporting portion 50, and thereby the valve body 43a abuts on the inner peripheral surface of the stationary portion 41A and comes in close contact with this inner peripheral surface, thus closing the opening of the stationary portion 41A. In addition, this second valve portion 43A is formed such that when the pressure in the space 44 has become higher than the pressure in the container 11A, the valve body 43a moves to the container 11A side, thereby releasing the opening of the stationary portion 41A and permitting communication between the space 44 and container 11A via the openings 50a of the supporting portion 50.

The container 11A is airtightly fixed to the base portion 21A. For example, a rigid, bottomed cylindrical cup, which has no flexibility, is used as the container 11A.

According to the syringe receptacle 1A with this structure, the same functions and advantageous effects as with the syringe receptacle 1 are obtained. By the air removing work of the syringe 200, the air in the syringe 200 can be discharged into the container 11A, and the air in the syringe 200 can be removed. Specifically, as illustrated in FIG. 11, the injection needle 212 is inserted into the spout portion 10A until the projection portions 223 of the coupling portion 221 abut on the inner peripheral surface of the first opening portion 31, and the distal end of the needle portion 222 is located in the space 44.

Next, the syringe receptacle 1 and syringe 200 are inclined such that the injection needle 212 is positioned upward, the plunger 211 is pushed into the barrel 210, and the air in the syringe 200 is discharged from the injection needle 212. Thereby, the air or the like is discharged into the space 44, and thus the pressure in the space 44 increases, the valve body 43a is pushed, and the second valve portion 43A enters the open state. Thereby, the space 44 communicates with the inside of the container 11A, and the air or the like in the space 44 moves into the container 11A until the pressure in the space 44 becomes equal to the pressure in the container 11A. If the air or the like in the space 44 moves into the container 11A, the second valve portion 43A seals the openings 50a by the restoring force thereof, and the space 44 and the inside of the container 11A are shut off from each other. In this manner, the syringe receptacle 1A can discharge the air or the like in the syringe 200 into the container 11A.

The syringe receptacle 1A, as described above, can safely and exactly discharge, with the simple structure, the air, which was sucked in the syringe 200 together with the medical fluid, from the syringe 200, without leaking the air or the like discharged from the syringe 200. It is thus possible to prevent the influence on the worker or the contamination in the surrounding due to the leak, etc. of the medical fluid.

As described above, according to the syringe receptacle 1A of the second embodiment of the present invention, a fluid such as air, which is discharged from the syringe 200, can be safely contained in the container 11A, and the manufacturing cost can be reduced.

Third Embodiment

Next, the structure of a syringe receptacle 1B according to a third embodiment of the present invention will be described with reference to FIG. 12 and FIG. 13.

FIG. 12 is a cross-sectional view illustrating the structure of the syringe receptacle 1B according to the third embodiment of the invention. FIG. 13 is a cross-sectional view illustrating the structure of a main part of the syringe receptacle 1B. Of the structure of the syringe receptacle 1B according the third embodiment, the same structural parts as the structural parts of the syringe receptacle 1 according to the above-described first embodiment and the syringe receptacle 1A according to the second embodiment are denoted by like reference numerals, and a detailed description thereof is omitted.

Like the above-described syringe receptacles 1 and 1A, the syringe receptacle 1B is used for storing air or the like, when a medical fluid was sucked in the syringe 200 and air included in the medical fluid is pushed out of the syringe 200.

Figure 13:
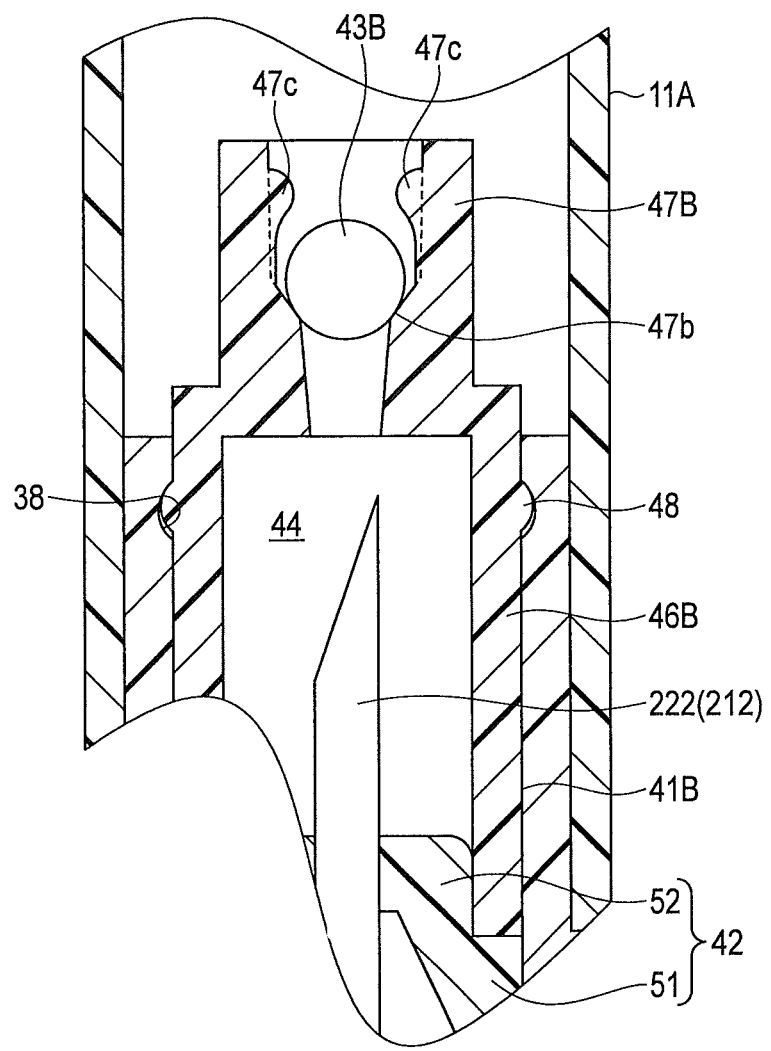
FIG. 13 is a cross-sectional view illustrating the structure of a main part of the syringe receptacle.

As illustrated in FIG. 12 to FIG. 13, the syringe receptacle 1B includes a spout portion 10B, a container 11A and a cover portion 12 (not shown in FIG. 12 or FIG. 13).

The spout portion 10B includes a base portion 21A which is formed in a cylindrical shape, and a valve portion 22B which is provided at an end portion of the base portion 21A. The base portion 21A is provided with a valve portion 22B at the other end portion thereof.

The valve portion 22B includes a stationary portion 41B which is fixed to the second opening portion 32A; a first valve portion 42; and a second valve portion 43B. The valve portion 22B is a check valve which is provided at the end portion of the base portion 21A. In addition, the valve portion 22B forms a space 44 which is sealed between the communication hole 33 and container 11A and communicates with the communication hole 33 and container 11A.

The stationary portion 41B is formed in a cylindrical shape with both ends opened, the stationary portion 41B having two different outside diameters and inside diameters. The stationary portion 41B includes a first stationary portion 46B which is formed to have an outside diameter which is equal to the inside diameter of the second opening portion 32A, and a second stationary portion 47B which is formed to have an inside diameter and an outside diameter, which are smaller than those of the first stationary portion 46B. In the first stationary portion 46B, an annular projection portion 48 is formed on a part of the outer peripheral surface thereof.

The second stationary portion 47B includes, on the inner peripheral surface thereof, a bearing surface portion 47b having an annular bearing surface which abuts on the second valve portion 43B, and includes a plurality of projections 47c which are provided on the inner peripheral surface of the second stationary portion 47B and restrict the movement of the second valve portion 43B. The second stationary portion 47B is formed such that the inside diameter thereof from the first stationary portion 46B to the bearing surface portion 47b is smaller than the inside diameter thereof from the bearing surface portion 47b to the end portion. The plural projections 47c are disposed at predetermined intervals, and form a gap between the outer surface of the second valve portion 43B and the inner peripheral surface of the second stationary portion 47B when the projections 47c restrict the movement of the second valve portion 43B.

The first valve portion 42 includes a disc-shaped first portion 51 which is formed to have an outside diameter that is substantially equal to or slightly greater than the inside diameter of the second opening portion 32A; and a columnar second portion 52 which is formed to have an outside diameter that is substantially equal to or slightly greater than the inside diameter of the first stationary portion 46B.

The second valve portion 43B is formed of a resin material or a metallic material in a spherical shape with a diameter which is less than the inside diameter of the second stationary portion 47B from the bearing surface portion 47b to the end portion. The second valve portion 43B abuts on the projections 47c, and thereby the movement toward the container 11A side is restricted.

The second valve portion 43B comes in contact with the bearing surface portion 47b in an annular fashion, thereby closing the opening of the second stationary portion 47B. In addition, the second valve portion 43B is formed such that when the pressure in the space 44 has become higher than the pressure in the container 11A, the second valve portion 43B moves to the container 11A side, thereby releasing the opening of the second stationary portion 47B and permitting communication between the space 44 and container 11A via the gap between the outer surface of the second valve portion 43B and the inner peripheral surface of the second stationary portion 47B.

According to the syringe receptacle 1B with this structure, the same functions and advantageous effects as with the syringe receptacle 1 are obtained. By the air removing work of the syringe 200, the valve portion 22B enters the open state. Thus, the air in the syringe 200 can be discharged into the container 11A, and the air in the syringe 200 can be removed. Specifically, as illustrated in FIG. 11, in the state in which the syringe receptacle 1B stands upright such that the second valve portion 43B comes in contact with the bearing surface portion 47b, the injection needle 212 is inserted into the spout portion 10B and the distal end of the needle portion 222 is located in the space 44.

Next, the plunger 211 is pushed into the barrel 210, and the air in the syringe 200 is discharged from the injection needle 212. Thereby, the air or the like is discharged into the space 44, and thus the pressure in the space 44 increases, the second valve portion 43B is pushed, and the second valve portion 43B enters the open state. Thereby, the space 44 communicates with the inside of the container 11A, and the air or the like in the space 44 moves into the container 11 until the pressure in the space 44 becomes equal to the pressure in the container 11. If the air or the like in the space 44 moves into the container 11A, the second valve portion 43B abuts on the bearing surface portion 47b by its own weight, and the space 44 and the inside of the container 11A are shut off from each other. In this manner, the syringe receptacle 1B can discharge the air or the like in the syringe 200 into the container 11A.

The syringe receptacle 1B, as described above, can safely and exactly discharge, with the simple structure, the air, which was sucked in the syringe 200 together with the medical fluid, from the syringe 200, without leaking the air or the like discharged from the syringe 200. It is thus possible to prevent the influence on the worker or the contamination in the surrounding due to the leak, etc. of the medical fluid.

As described above, according to the syringe receptacle 1B of the third embodiment of the present invention, a fluid such as air, which is discharged from the syringe 200, can be safely contained in the container 11A, and the manufacturing cost can be reduced.

Fourth Embodiment

Hereinafter, the structure of a syringe receptacle 100 according to a fourth embodiment of the present invention will be described with reference to FIG. 14 and FIG. 15.

Figure 14:
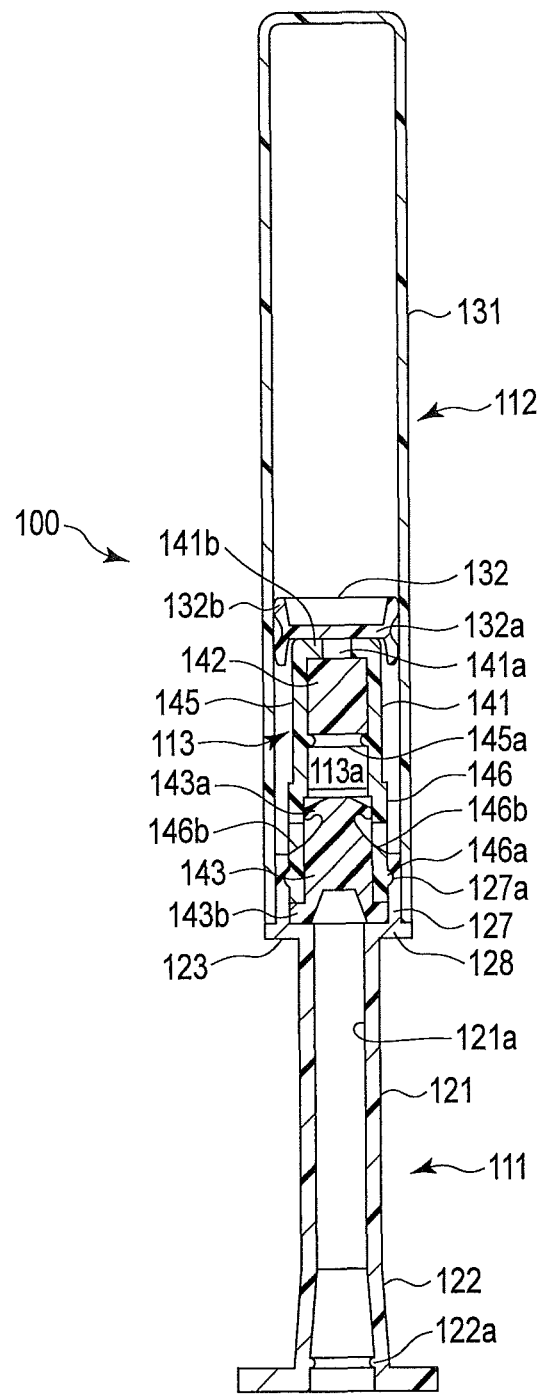
FIG. 14 is a cross-sectional view illustrating the structure of a syringe receptacle according to a fourth embodiment of the present invention.

FIG. 14 is a cross-sectional view illustrating the structure of the syringe receptacle 100 according to the fourth embodiment of the present invention. FIG. 15 is a cross-sectional view illustrating the structure of the syringe receptacle 100, and illustrating a state of use, in which the injection needle 212 of the syringe 200 is pierced.

Figure 15:
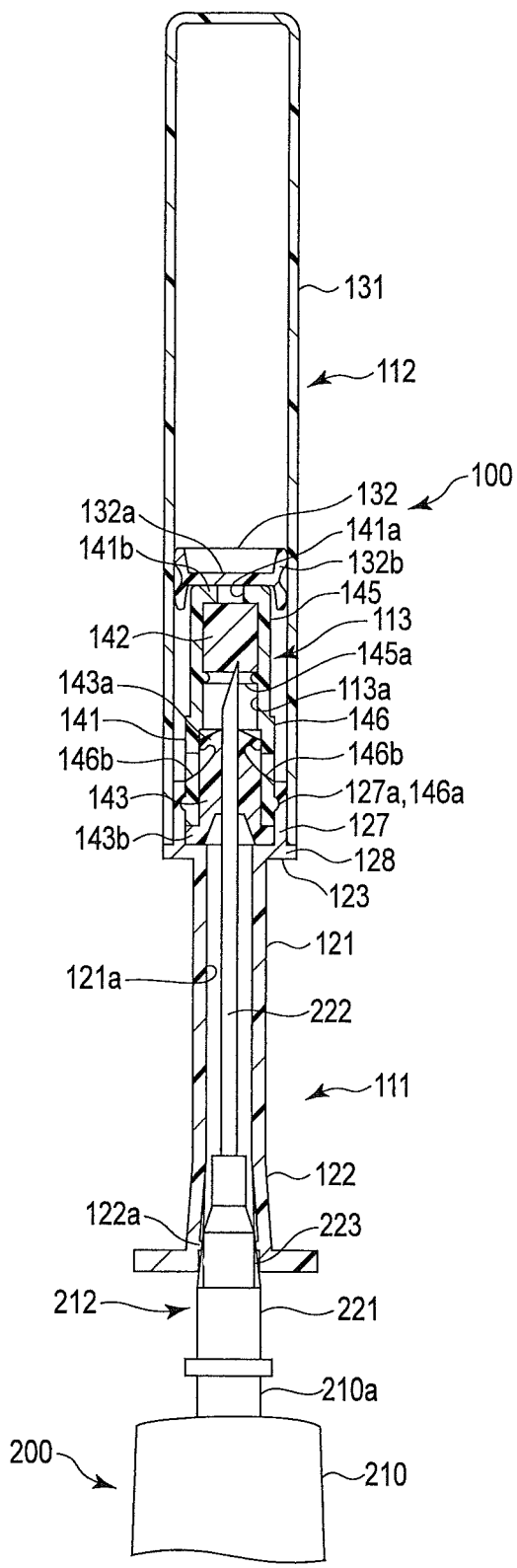
FIG. 15 is a cross-sectional view illustrating the structure of the syringe receptacle.

As illustrated in FIG. 14 and FIG. 15, the syringe receptacle 100 includes a base portion 111, a reservoir portion 112 and a valve member 113. The syringe receptacle 100 is a reservoir container configured such that a fluid, which is unnecessary when the syringe is used, and which was discharged from the syringe 200, is stored in the reservoir portion 112, and the reservoir portion 112 is sealed by the valve member 113. The fluid is, for instance, air, air (gas) including a medical fluid, or a medical fluid, which is an injection solution in the syringe 200.

In the meantime, as illustrated in FIG. 8 and FIG. 15, the syringe 200, which is used for the syringe receptacle 100, includes a barrel 210 which is formed in a cylindrical shape and has a distal end portion 210a with a small diameter; a plunger which is inserted in the barrel 210; and an injection needle 212 provided on the distal end portion 210a of the barrel 210.

The barrel 210 is a cylinder in which the plunger is reciprocally movable. The barrel 210, together with the plunger, forms within the syringe 200 a space which can store a medical fluid. The injection needle 212 is detachably provided on the distal end portion 210a of the barrel 210.

As illustrated in FIG. 2, the injection needle 212 is formed of a metallic material or a resin material, and includes a coupling portion 221 which is fixed to the distal end portion 210a of the barrel 210, and a needle portion 222 provided on the coupling portion 221.

The coupling portion 221 is formed in a cylindrical shape having a plurality of different outside diameters, and is formed to be engageable with the distal end portion 210a of the barrel 210. In addition, the needle portion 222 is put in close contact with, and fixed to, the inner peripheral surface of the coupling portion 221. The coupling portion 221 includes, for example, on a part of the outer peripheral surface thereof, a plurality of projection portions 223 which are provided to extend along the longitudinal direction of the coupling portion 221 and which have outer surfaces that are inclined relative to the axis of the coupling portion 221.

The needle portion 222 is formed in such a cylindrical shape that a fluid can move in the inside of the needle portion 222. A distal end of the needle portion 222 is formed at such an acute angle as to be capable of piercing. The plural projection portions 223 are disposed, for example, at equal intervals at four locations on the outer peripheral surface of the coupling portion 221.

The base portion 111 includes a cylindrical body portion 121, a first stationary portion 122 provided at one end portion of the body portion 121, and a second stationary portion 123 provided at the other end portion of the body portion 121.

The body portion 121 includes a communication hole 121a which is formed to have such an inside diameter that the needle portion 222 of the injection needle 212 is insertable. The first stationary portion 122 is formed such that the inside diameter thereof is gradually increased from the body portion 121 toward the end portion. The first stationary portion 122 includes an annular projection portion 122a on the inner peripheral surface thereof. The first stationary portion 122 is formed such that the coupling portion 221 of the injection needle 212 is insertable and the projection portion 122a is engageable with the coupling portion 221. The first stationary portion 122 is formed to be capable of preventing excessive insertion of the injection needle 212, by the projection portion 122a being engaged with the coupling portion 221.

The second stationary portion 123 includes a cylinder portion 127 which is engageable with the valve member 113, and a flange portion 128 to which the reservoir portion 112 can be fixed. An annular recess portion 127a is formed in the inner peripheral surface of the cylinder portion 127. The cylinder portion 127 is formed to have an outside diameter which is substantially equal to the inside diameter of the reservoir portion 112. The flange portion 128 is an annular projection projecting from the side surface of the cylinder portion 127.

The reservoir portion 112 includes a cylinder 131 having a bottomed cylindrical shape, and a piston 132 which is movably formed within the cylinder 131. The cylinder 131 is formed to have an inside diameter which is greater than the outside diameter of the valve member 113 and is substantially equal to the outside diameter of the cylinder portion 127.

The cylinder 131 has its opening end portion inserted over the cylinder portion 127 and airtightly fixed to the flange portion 128. For example, the cylinder 131 is airtightly fixed to the flange portion 128 by adhesion by an adhesive, or by fusion bonding by heat. The cylinder 131 is formed of a light-transmissive resin material, for instance, a transparent resin material which enables visual recognition of the piston 132.

The piston 132 includes a disc portion 132a, and a seal portion 132b which is provided on an outer peripheral edge of the disc portion 132a. The seal portion 132b is formed to be capable of coming in close contact with the inner peripheral surface of the cylinder 131, and to be slidable on this inner peripheral surface. The seal portion 132b is composed of, for example, two annular projections such that the seal portion 132b can be put in contact with the inner peripheral surface of the cylinder 131 at two locations in the axial direction. This piston 132 is formed to be capable of dividing the inside of the cylinder 131 into two spaces, by the seal portion 132b being put in close contact with the inner peripheral surface of the cylinder 131.

The valve member 113 includes an outer shell body 141 having a bottomed cylindrical shape, a stopper body 142, and a valve body 143. The valve member 113 is formed to be capable of airtightly shutting off the base portion 111 and reservoir portion 112 from each other.

The outer shell body 141 is formed to have two different inside diameters, and an end face portion 141b having an opening portion 141a is formed at the smaller-diameter-side end portion. Specifically, the outer shell body 141 includes a cylindrical first accommodation portion 145 provided on the end face portion 141b side, and a cylindrical second accommodation portion 146 formed to have an inside diameter which is greater than the inside diameter of the first accommodation portion 145. The outer shell body 141 is formed of a light-transmissive resin material, for instance, a transparent resin material which enables visual recognition of the injection needle 212 which is inserted.

The first accommodation portion 145 includes an annular projection portion 145a on the inner peripheral surface thereof, at a substantially middle position between the end face portion 141b and the second accommodation portion 146. The first accommodation portion 145 is formed to be capable of accommodating the stopper body 142 between the projection portion 145a and the end face portion 141b.

The second accommodation portion 146 is formed to have an end portion opened, and to have an outside diameter which is substantially equal to the inside diameter of the cylinder portion 127. An annular projection portion 146a, which is engaged with the recess portion 127a of the cylinder portion 127, is formed on the outer peripheral surface of the second accommodation portion 146. A plurality of opening portions 146b are formed in a part of the outer peripheral surface of the second accommodation portion 146.

The second accommodation portion 146 is formed such that the length from the projection portion 146a to the opening end portion thereof is less than the length from the recess portion 127a of the cylinder portion 127 to the end portion on the body portion 121 of the cylinder portion 127. Specifically, when the second accommodation portion 146 is engaged with the cylinder portion 127, and the projection portion 146a is engaged with the recess portion 127a, the end portion of the second accommodation portion 146 is opposed to the end portion of the cylinder portion 127 with a predetermined gap.

The stopper body 142 is an elastic body formed of a resin material such as a natural rubber, a synthetic rubber or a foamed material. The stopper body 142 is formed in a columnar shape, and formed to have an outside diameter which is slightly larger than the inside diameter of the first accommodation portion 145. The stopper body 142 is engaged in the first accommodation portion 145. Thereby, the stopper body 142 is tightly accommodated between the end face portion 141b and the projection portion 145a of the first accommodation portion 145, and the stopper body 142 is formed to be capable of closing the opening portion 141a of the end face portion 141b.

The valve body 143 is an elastic body formed of a resin material such as a natural rubber, a synthetic rubber or a foamed material. The valve body 143 is provided in the second accommodation portion 146, thereby closing the communication hole 121a and the inside of the outer shell body 141.

The valve body 143 is formed in a columnar shape, and a distal-end side thereof is reduced in diameter, thereby creating a predetermined gap from the inner peripheral surface of the second accommodation portion 146, in which the openings 146b are formed. In addition, a disc-shaped movable valve 143a, which is in close contact with the inner peripheral surface of the second accommodation portion 146, is formed at a distal end of the valve body 143. Furthermore, an annularly projecting flange portion 143b, which is disposed in the gap between the end portion of the cylinder portion 127 and the end portion of the second accommodation portion 146, is formed on a rear-end side of the valve body 143.

In this valve member 113, the stopper body 142 and valve body 143 are provided in the outer shell body 141, a space 113a in the outer shell body 141 and the reservoir portion 112 are shut off from each other, and the space 113a in the outer shell body 141 and the communication hole 121a are shut off from each other, thereby forming the sealed space 113a. In addition, in the valve member 113, when the pressure in the space 113a becomes higher than the pressure in the reservoir portion 112, the movable valve 143a of the valve body 143 deforms and the movable valve 143a is spaced apart from the inner peripheral surface of the second accommodation portion 146. Thereby, the valve member 113 is formed to be capable of establishing communication between the space 113a and the space in the reservoir portion 112, via the space between the outer peripheral surface on the distal end side of the valve body 143 and the inner peripheral surface of the second accommodation portion 146, and via the opening portions 146b of the second accommodation portion 146.

Next, a manufacturing method of the syringe receptacle 100 with the above-described structure is described.

To begin with, the stopper body 142 is engaged and disposed in the first accommodation portion 145 of the outer shell body 141. Then, the valve body 143 is engaged and disposed in the second accommodation portion 146. Thereby, the valve member 113 is constituted. Next, the second accommodation portion 146 is inserted in the cylinder portion 127 of the base portion 111, and the projection portion 146a is engaged in the recess portion 127a. Since the flange portion 143b of the valve body 143 lies between the cylinder portion 127 and outer shell body 141, the cylinder portion 127 and outer shell body 141 are airtightly and integrally assembled.

Next, the reservoir portion 112, which is configured such that the piston 132 is inserted in the cylinder 131, is inserted over the cylinder portion 127 and airtightly adhered or fusion-bonded. Thereby, the base portion 111 and reservoir portion 112 are airtightly and integrally assembled.

Subsequently, a tube, which is connected to a suction device such as a vacuum pump, is pierced from the base portion 111 into the stopper body 142 and valve body 143. Thereafter, the suction device is driven, and air in the reservoir portion 112 is sucked from the opening portion 141a which is formed in the end face portion 141b of the outer shell body 141 of the valve member 113, and thus the piston 132 is moved until coming in contact with the end face portion 141b of the outer shell body 141. By these fabrication steps, the syringe receptacle 100 is manufactured.

Next, a method of use of the syringe receptacle 100 with the above-described structure is described.

To begin with, a medical fluid is filled in the syringe 200. Specifically, when a medical fluid is sucked from an ampoule into the syringe 200, a worker inserts the plunger into the barrel 210 of the syringe 200 down to the bottom dead point, and inserts the injection needle into the ampoule. In this state, the plunger is moved up to the top dead point. Thereby, the medical fluid is sucked into the space which is formed within the syringe 200 by the barrel 210 and plunger.

In the suction of the medical fluid, if air is also sucked in the syringe 200 or an excess medical fluid is sucked, an unnecessary fluid is discharged into the syringe receptacle 100. Specifically, as illustrated in FIG. 15, the needle portion 222 of the injection needle 212 is pierced into the valve body 143, and the injection needle 212 is inserted into the base portion 111 until the projection portions 223 of the coupling portion 221 abut on the projection portion 122a of the first stationary portion 122 of the base portion 111 and the distal end of the needle portion 222 is located in the space 113a of the valve member 113.

Next, the plunger is pushed to the bottom dead point, and the unnecessary fluid is discharged from the syringe 200 into the space 113a. At this time, the pressure in the space 113a increases due to the unnecessary fluid discharged from the syringe 200. Thereby, the movable valve 143a of the valve body 143 opens, the space 113a communicates with the inside space of the reservoir portion 112, and the unnecessary fluid moves into the reservoir portion 112.

At this time, in accordance with the amount of the fluid flowing into the reservoir portion 112, the pressure in the reservoir portion 112 increases and the piston 132 moves. If the piston 132 moves and the discharge of the fluid from the syringe 200 stops, a pressure difference between the space 113a and the reservoir portion 112 decreases to zero, the movable valve 143a restores to the original position, and the space 113a and the inside space of the reservoir portion 112 are shut off from each other by the movable valve 143a.

Next, the user pulls out the injection needle 212 from the valve body 143. At this time, the valve body 143 restores, by the restoring force, gradually from the part from which the needle portion 222 was pulled out, and the hole formed by the piercing is closed. Thus, the space 113a is shut off, and the discharged fluid can be made to stay in the reservoir portion 112 and space 113a. In this manner, the unnecessary fluid in the syringe 200 can be discharged, and the syringe 200 is made ready for use.

In addition, at a time of discarding the injection needle 212 after the syringe 200 was used, the needle portion 222 of the injection needle 212 is pierced into the valve body 143. After the projection portions 223 of the coupling portion 221 abut on the projection portion 122a of the first stationary portion 122, the injection needle 212 is further press-inserted. Thereby, the distal end of the injection needle 212 is inserted beyond the space 113a and is pierced into the stopper body 142. At this time, the opening at the distal end of the needle portion 222 is located in the stopper body 142, the opening of the needle portion 222 is closed by the stopper body 142, and the valve body 143 is put in close contact with the periphery of the needle portion 222. Thus, the space 113a is shut off from the outside air. Therefore, the injection needle 212 and syringe receptacle 100 can be discarded in the state in which the fluid remaining in the needle portion 222 does not leak to the outside air and is retained in the needle portion 222.

According to the syringe receptacle 100 with the above-described structure, an unnecessary fluid can be discharged from the syringe 200 into the reservoir portion 112. In addition, even when the fluid to be discharged is not merely air in the syringe 200 but also the air including a medical fluid, or an excess medical fluid, the discharged fluid moves from the space 113a of the valve member 113 into the reservoir portion 112 and can be stored in the reservoir portion 112. Furthermore, even when the discharged unnecessary fluid does not move into the reservoir portion 112 and remains in the space 113a, the valve body 143 seals the space 113a and, therefore, there is no fear that the discharged fluid or the like leaks to the outside of the syringe receptacle 100.

In this manner, the syringe receptacle 100 can safely and exactly discharge the unnecessary fluid in the syringe 200 from the syringe 200, without leaking the fluid discharged from the syringe 200. It is thus possible to prevent the influence on the worker or the contamination in the surrounding due to the leak, etc. of the medical fluid.

Additionally, in the syringe receptacle 100, the stopper body 142 and valve body 143 are configured as stoppers formed of an elastic body. Thus, there is no need to additionally close the hole that was formed by the piercing of the needle portion 222 and the tube for sucking the air in the reservoir portion 112 at the time of manufacture.

Additionally, when the injection needle 212 is discarded, the syringe receptacle 100 and injection needle 212 can be discarded as one piece by piercing the injection needle 212 into the stopper body 142 and valve body 143. Moreover, in this case, since the opening at the distal end of the needle portion 222 is disposed in the stopper body 142, the opening at the distal end of the needle portion 222 is closed and the valve body 143 is put in close contact with the periphery of the needle portion 222. It is thus possible to prevent leak to the outside of the medical fluid in the needle portion 222 or the fluid in the space 113a. Besides, since the distal end of the needle portion 222 is disposed in the stopper body 142, there is no fear that the distal end of the needle portion 222 comes in contact with the user, etc.

Additionally, the syringe receptacle 100 can be manufactured with such a simple configuration that the elastically deformable stopper body 142 and valve body 143 are provided on a primary side and a secondary side of the space 113a, the base portion 111, reservoir portion 112 and valve member 113 are fixed, and the piston 132 is moved to the valve member 113 side by sucking air in the reservoir portion 112. Thus, the productivity of the syringe receptacle 100 can be enhanced, and the manufacturing cost can be reduced. In particular, since the syringe receptacle 100 is discarded after use, the running cost in the case of use in medical practice, etc. can be reduced.

Besides, in the syringe receptacle 100, the air, etc. discharged from the syringe 200 is contained in the reservoir portion 112 and the space 113a, which are shut off from the outside by the valve body 143. Therefore, high safety can be ensured.

As described above, according to the syringe receptacle 100 of the fourth embodiment of the present invention, a fluid such as air or a medical fluid, which is discharged from the syringe 200, can be safely contained, and the productivity can be enhanced at low cost.

Fifth Embodiment

Next, the structure of a syringe receptacle 100A according to a fifth embodiment of the present invention will be described with reference to FIG. 16.

FIG. 16 is a cross-sectional view illustrating the structure of the syringe receptacle 100A according to the fifth embodiment of the invention. Incidentally, of the structure of the syringe receptacle 100A according the fifth embodiment, the same structural parts as the structural parts of the syringe receptacle 100 according to the above-described fourth embodiment are denoted by like reference numerals, and a detailed description thereof is omitted.

As illustrated in FIG. 16, the syringe receptacle 100A includes a base portion 111, a reservoir portion 112A and a valve member 113. The syringe receptacle 100A is a reservoir container configured such that a fluid, such as air, air (gas) including a medical fluid, or a medical fluid, which is unnecessary when the syringe is used, and which was discharged from the syringe 200, is stored in the reservoir portion 112A, and the reservoir portion 112A is sealed by the valve member 113.

The reservoir portion 112A includes a cylinder 131A having a bottomed cylindrical shape, and a piston 132 which is movably formed within the cylinder 131A. The cylinder 131A is formed to have an inside diameter which is greater than the outside diameter of the valve member 113 and is substantially equal to the outside diameter of the cylinder portion 127.

The cylinder 131A has its opening end portion inserted over the cylinder portion 127 and airtightly fixed to the flange portion 128. For example, the cylinder 131A is airtightly fixed to the flange portion 128 by adhesion by an adhesive, or by fusion bonding by heat. In addition, the cylinder 131A has an opening portion 131a formed at an end portion opposed to the opening end portion.

According to the syringe receptacle 100A with this structure, like the above-described syringe receptacle 100, a fluid such as air or a medical fluid, which is discharged from the syringe 200, can be safely contained, and the productivity can be enhanced at low cost.

In addition, in the syringe receptacle 100A which is configured such that the opening portion 131a is provided at the end portion of the cylinder 131A, the space, which is formed by the cylinder 131A and piston 132 and which does not communicate with the space 113a of the valve member 113, communicates with the outside space of the cylinder 131. Thus, the atmospheric pressure is maintained without the piston 132 compressing the air in the space on one side (on a side where the opening portion 131a is formed) which is formed between the piston 132 and the cylinder 131A.

Therefore, as illustrated in FIG. 16, the piston 132 can move to the end portion of the cylinder 131A, and a greater amount of fluid can be contained.

Furthermore, the piston 132 can maintain at the atmospheric pressure the pressure in the space 113a of the valve member 113 and in the space which communicates with the space 113a and is formed by the piston 132 and the cylinder 131A. Therefore, it is possible to prevent the pressure of the space 113a from becoming higher than the atmospheric pressure, and to ensure higher safety.

As described above, according to the syringe receptacle 100A of the fifth embodiment of the present invention, a fluid such as air or a medical fluid, which is discharged from the syringe 200, can be safely contained, and the productivity can be enhanced at low cost.

Sixth Embodiment

Next, the structure of a syringe receptacle 100B according to a sixth embodiment of the present invention will be described with reference to FIG. 17.

Figure 17:
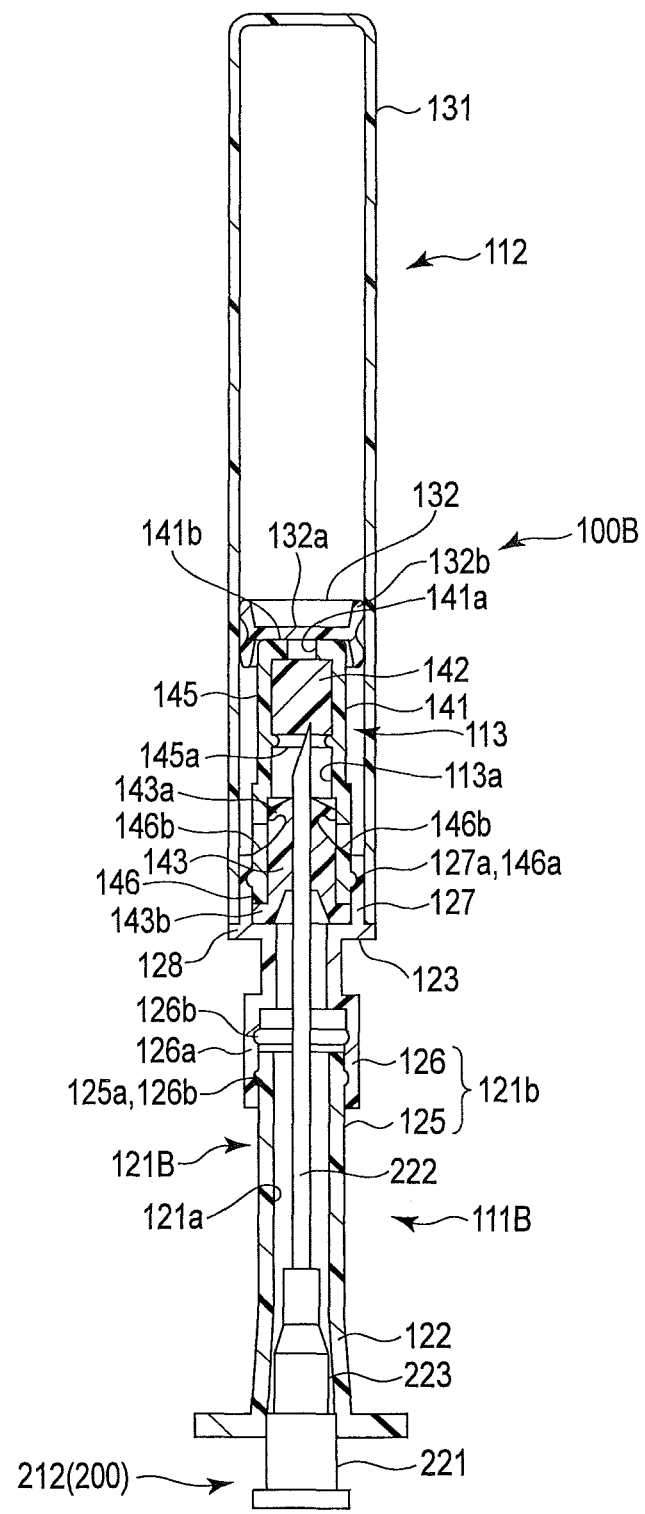
FIG. 17 is a cross-sectional view illustrating the structure of a syringe receptacle according to a sixth embodiment of the present invention.

FIG. 17 is a cross-sectional view illustrating the structure of the syringe receptacle 100B according to the sixth embodiment of the invention. Incidentally, of the structure of the syringe receptacle 100B according the sixth embodiment, the same structural parts as the structural parts of the syringe receptacle 100 according to the above-described fourth embodiment are denoted by like reference numerals, and a detailed description thereof is omitted.

As illustrated in FIG. 17, the syringe receptacle 100B includes a base portion 111B, a reservoir portion 112 and a valve member 113. The syringe receptacle 100B is a reservoir container configured such that a fluid, such as air, air (gas) including a medical fluid, or a medical fluid, which is unnecessary when the syringe is used, and which was discharged from the syringe 200, is stored in the reservoir portion 112, and the reservoir portion 112 is sealed by the valve member 113.

The base portion 111B includes a cylindrical body portion 121B, a first stationary portion 122 provided at one end portion of the body portion 121B, and a second stationary portion 123 provided at the other end portion of the body portion 121B.

The body portion 121B is formed to have such an inside diameter that the needle portion 222 of the injection needle 212 is insertable. The body portion 121B includes a first body portion 125, and a second body portion 126 which is engaged with and fixed to the first body portion 125. The body portion 121B constitutes, by the first body portion 125 and second body portion 126, an adjusting portion 121b which can change the length in the axial direction of the body portion 121B.

The first body portion 125 is formed in a cylindrical shape, and is formed to have such an inside diameter that the needle portion 222 of the injection needle 212 is insertable. The first body portion 125 includes a first stationary portion 122 at one end portion thereof, and includes an annular projection portion 125a on an outer peripheral surface of the other end portion thereof.

The second body portion 126 is formed in a cylindrical shape, and is formed to have such an inside diameter that the needle portion 222 of the injection needle 212 is insertable. The second body portion 126 includes, at one end portion thereof, an engaging portion 126a in which the end portion of the first body portion 125, where the projection portion 125a is formed, can be inserted. The second body portion 126 includes a second stationary portion 123 at the other end portion thereof.

The engaging portion 126a is formed in a cylindrical shape, and is formed to have an inside diameter which is substantially equal to the outside diameter of the first body portion 125. In addition, the engaging portion 126a includes, in the inner peripheral surface thereof, a plurality of annular recess portions 126b, or two annular recess portions 126b in this embodiment, which are engageable with the projection portion 125a of the first body portion. The two recess portions 126b are spaced apart by a predetermined distance, and are disposed in parallel.

This base portion 111B is assembled as one piece, by the first body portion 125 being inserted into the engaging portion 126a of the second body portion 126, and by the projection portion 125a being engaged with the recess portion 126b. The base portion 111B forms a communication hole 121a by the first body portion 125 and second body portion 126.

In addition, by the projection portion 125a being engaged with one of the recess portions 126b, to be more specific, the recess portion 126b on the one end portion side of the second body portion 126, the base portion 111B is formed to have such a length that the opening at the distal end of the needle portion 222 can be disposed in the space 113a of the valve member 113 when the injection needle 212 is inserted. Besides, by the projection portion 125a being engaged with the other recess portion 126b, to be more specific, the recess portion 126b on the other end portion side of the second body portion 126, the base portion 111B is formed to have such a length that the opening at the distal end of the needle portion 222 can be disposed in the stopper body 142 when the injection needle 212 is inserted. In this manner, the base portion 111B is formed such that the length in the axial direction thereof can be changed by the adjusting portion 121b which is composed by the projection portion 125a of the first body portion 125 and the engaging portion 126a having the plural recess portions 126b.

According to the syringe receptacle 100B with this structure, like the above-described syringe receptacle 100, a fluid such as air or a medical fluid, which is discharged from the syringe 200, can be safely contained, and the productivity can be enhanced at low cost.

In addition, in the syringe receptacle 100B, the base portion 111B is composed of the first body portion 125 and second body portion 126, and the projection portion 125a of the first body portion 125 is engaged with any one of the plural recess portions 126b provided on the second body portion 126. Thereby, the length in the axial direction of the base portion 111B can be changed.

Thus, after the syringe receptacle 100B was used, if the injection needle 212 is pierced into the stopper body 142 and is discarded together with the syringe receptacle 100B, the first body portion 125 is pushed into the second body portion 126, and the projection portion 125a is engaged with the next recess portion 126b. Thereby, the injection needle 212 can easily be pierced into the stopper body 142. In short, there is no need to press-insert the injection needle 212. Therefore, workability is enhanced when the injection needle 212 is discarded together with the syringe receptacle 100B.

Furthermore, the syringe receptacle 100B may include not the two recess portions 126b, but three or more recess portions 126b. When the lengths of needle portions 222 of syringes 212, which are used, are different, the syringe receptacle 100B may include a plurality of recess portions 126b with widths corresponding to the lengths of the needle portions 222. Thereby, the syringe receptacle 100B can be used commonly for injection needles 212 with needle portions 222 having different lengths.

As described above, according to the syringe receptacle 100B of the sixth embodiment of the present invention, a fluid such as air or a medical fluid, which is discharged from the syringe 200, can be safely contained, and the productivity can be enhanced at low cost.

Seventh Embodiment

Next, the structure of a syringe receptacle 100C according to a seventh embodiment of the present invention will be described with reference to FIG. 18.

Figure 18:
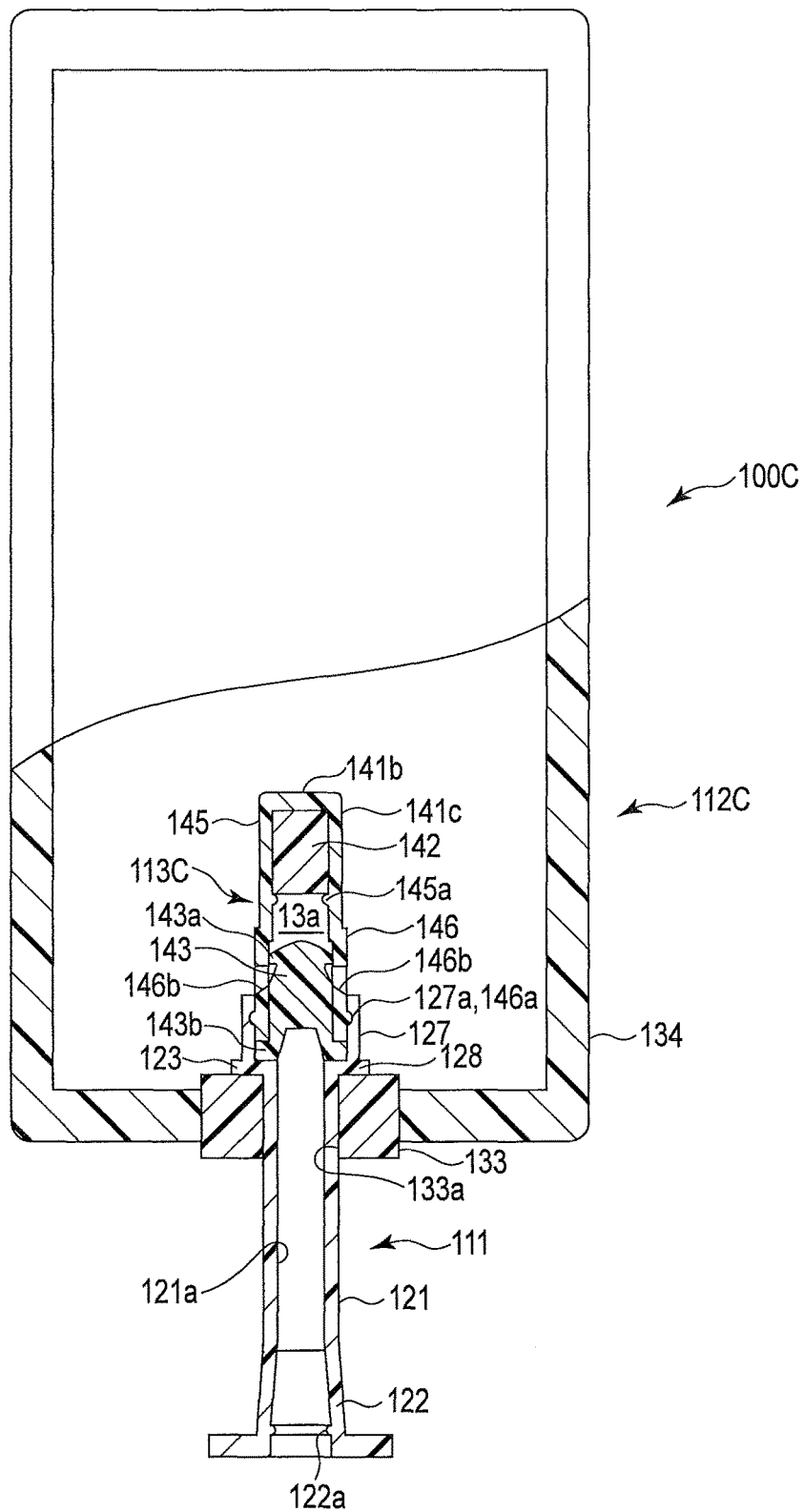
FIG. 18 is a cross-sectional view illustrating the structure of a syringe receptacle according to a seventh embodiment of the present invention.

FIG. 18 is a cross-sectional view illustrating the structure of the syringe receptacle 100C according to the seventh embodiment of the invention. Incidentally, of the structure of the syringe receptacle 100C according the seventh embodiment, the same structural parts as the structural parts of the syringe receptacle 100 according to the above-described fourth embodiment are denoted by like reference numerals, and a detailed description thereof is omitted.

As illustrated in FIG. 18, the syringe receptacle 100C includes a base portion 111, a reservoir portion 112C and a valve member 113C. The syringe receptacle 100C is a reservoir container configured such that a fluid, such as air, air (gas) including a medical fluid, or a medical fluid, which is unnecessary when the syringe is used, and which was discharged from the syringe 200, is stored in the reservoir portion 112C, and the reservoir portion 112C is sealed by the valve member 113C.

The reservoir portion 112 includes an attachment portion 133 provided on the body portion 121, and a container 134 with flexibility, which is airtightly fixed to the attachment portion 133.

The attachment portion 133 includes a hole portion 133a, and is formed such that the hole portion 133a is airtightly fixed to the body portion 121, and the container 134 can be airtightly fixed to the outer surface of the attachment portion 133. The attachment portion 133 is formed to be fixable to the container 134, for example, by fusion-bonding to the container 134.

The container 134 is a so-called pouch, which is formed by attaching films which are formed of a resin material with flexibility. A peripheral part of the container 134 is airtightly adhered, and the container 134 is airtightly adhered to the attachment portion 133, and thereby the container 134 is formed with the inside thereof sealed. The container 134 is formed such that the valve member 113C can be disposed within the container 134. The container 134 is formed of a light-transmissive resin material, for instance, a transparent resin material which enables visual recognition of the valve member 113C.

The valve member 113C includes an outer shell body 141C having a bottomed cylindrical shape, a stopper body 142, and a valve body 143. The valve member 113C is formed to be capable of airtightly shutting off the base portion 111 and reservoir portion 112C from each other.

The outer shell body 141C is formed to have two different inside diameters, and an end face portion 141b is formed at the smaller-diameter-side end portion. Specifically, the outer shell body 141C includes a cylindrical first accommodation portion 145 provided on the end face portion 141b side, and a cylindrical second accommodation portion 146 formed to have an inside diameter which is greater than the inside diameter of the first accommodation portion 145. The outer shell body 141C is configured not to include the above-described opening portion 141a of the outer shell body 141 at the end face portion 141b. The outer shell body 141C is formed of a light-transmissive resin material, for instance, a transparent resin material which enables visual recognition of the injection needle 212 which is inserted.

According to the syringe receptacle 100C with this structure, like the above-described syringe receptacle 100, a fluid such as air or a medical fluid, which is discharged from the syringe 200, can be safely contained, and the productivity can be enhanced at low cost.

In addition, by using the container 134 with flexibility, the syringe receptacle 100C can be manufactured without piercing the tube of the sucking device into the stopper 142 and valve body 143 at the time of manufacture and sucking the air within the container 134. Moreover, the structure of the reservoir portion 112C is simple. Therefore, the manufacturing cost of the syringe receptacle 100C can be reduced.

As described above, according to the syringe receptacle 100C of the seventh embodiment of the invention, a fluid such as air or a medical fluid, which is discharged from the syringe 200, can be safely contained, and the productivity can be enhanced at low cost.

In the meantime, the present invention is not limited to the above-described embodiments. In the above-described examples, the configuration in which a medical fluid is supplied from an ampoule into the syringe 200 was described. However, the invention is not limited to this configuration, and such a configuration may be adopted that a medical fluid is supplied from a vial.

Additionally, in the above-described examples, the configuration in which the first opening portion 31 is provided with the projections 36 was described. However, the invention is not limited to this configuration. In the case of a configuration in which the injection needle 212 of the syringe 200 does not include the projection portions 223, such a configuration may be adopted that the first opening portion 31 does not include the projection portions 36.

Additionally, in the above-described examples, the configuration in which the second valve 43 has a tubular shape, the configuration in which the second valve portion 43A has a disc shape, and the configuration in which the second valve portion 43B has a spherical shape were described. However, the invention is not limited to these configurations, and the second valve portion may have a plate shape or other shape, if sealing can be made between the space 44 and the container 11, 11A.

However, the above-described configurations of the second valve portions 43, 43A and 43B are desirable since the assembly is easy and the configurations are simple.

In addition, as regards the volume of the space 44, although no particular description is given, if the opening/closing of the second valve portion 43 is taken into account, it is preferable that the volume is small. The space 44 can properly be set to have an as small as possible shape, such that the distal end of the needle portion 222, which penetrates the first valve portion 42, can be disposed in the space 44. Moreover, as regards the space 44 in the above-described second embodiment, the length of the space 44 in the axial direction may be decreased in order to reduce the volume of the space 44. Thereby, not only the volume can be reduced, but also the distal end of the injection needle 212 can be inserted in the supported portion 43b of the second valve portion 43A, when the injection needle 212 is discarded together with the syringe receptacle 1B. Thereby, it becomes possible to prevent the space 44 from communicating with the outside air via the injection needle 212.

Additionally, in the above-described examples, the configuration in which the first valve portion 42 is formed in a columnar shape was described. However, for example, the first valve portion 42 may be configured to include a hole portion, which is closed at a normal time, for guiding the piercing of the needle portion 222 of the injection needle 212.

Furthermore, in the above-described examples, the configuration in which the container 11 with flexibility is used for the syringe receptacle 1, and the configuration in which the container 11A with no flexibility is used for the syringe receptacle 1A, 1B, were described. However, the invention is not limited to these configurations. Such a configuration may be adopted that the container 11A is used for the syringe receptacle 1, or the container 11 is used for the syringe receptacle 1A, 1B. Besides, other various modifications may be implemented without departing from the spirit of the present invention.

Additionally, in the above-described examples, the description was given of the configuration of the syringe receptacle 100B, in which the tube of the sucking device is pierced into the stopper 142 at the time of manufacture and the air in the reservoir portion 113 is sucked. However, the invention is not limited to this configuration. A configuration may be adopted in which, in the manufacture, the piston 132 is disposed in advance at such a position as to come in contact with the outer shell body 141 of the cylinder 131.

Additionally, in the above-described examples, the description was given of the configuration of the syringe receptacle 100B, in which the adjusting portion 121b, which can change the length of the base portion 111B, is composed by the projection portion 125a provided on the first body portion 125 and the engaging portion 126a having the plural recess portions 126b provided on the second body portion 126. However, the invention is not limited to this configuration. For example, such a configuration may be adopted that a male screw portion is provided on the outer peripheral surface of the first body portion 125, and a female screw portion is provided on the inner peripheral portion of the engaging portion 126a of the second body portion 126. Besides, other embodiments may be configured to include such adjusting portions.

Additionally, in the above-described examples, the syringe receptacle 100C is configured such that there is no need to provide the end face portion 141b of the outer shell body 141 with the opening portion 141a for sucking the air in the reservoir portion 112C. Thus, the syringe receptacle 100C may be configured not to include the stopper body 142, when the syringe receptacle 100C is used for such a purpose of use that when the syringe receptacle 100C is discarded, the injection needle 212 is not discarded together, and only the syringe receptacle 100C is discarded. By adopting this configuration, the manufacturing cost can be further reduced.

Additionally, the above-described syringe receptacle 100C is configured not to include the opening portion 141a in the end face portion 141b. However, such a configuration may be adopted that the opening portion 141a is provided, and the air in the reservoir portion 112C is sucked by the suction device after the manufacture. Besides, other various modifications may be implemented without departing from the spirit of the present invention.

What is claimed is:
1. A syringe receptacle comprising:
a base portion including a communication hole formed such that an injection needle of a syringe is insertable;
a container airtightly provided on the base portion;

a space forming portion provided on the base portion and forming a space which is connected to the communication hole and an inside of the container;

a first valve portion provided between the communication hole and the space, and configured to restrict a movement of a fluid from the space to the communication hole; and a second valve portion provided between the space and the inside of the container, and configured to restrict a movement of the fluid from the inside of the container to the space;

wherein:

the space forming portion is formed in a cylindrical shape with one end closed, and includes an opening in a part of an outer peripheral surface thereof;

the first valve portion is a stopper configured to close the communication hole and an opening of the space, the stopper being formed of a resin material which is pierceable by the injection needle;

the second valve portion is formed to be capable of closing the opening, and to be capable of releasing the opening when a pressure in the space is higher than a pressure in the container;

the base portion includes, at a first end portion thereof, a first end portion opening formed such that the space forming portion is insertable therein, and includes in an outer peripheral surface thereof an opening which is opposed to the opening of the space forming portion; and the second valve portion is formed in an elastically deformable tubular shape, and is configured to cover, by being inserted over the base portion, the opening of the base portion and the opening of the space forming portion.

2. The syringe receptacle of claim 1, wherein the injection needle includes a coupling portion which is formed in a truncated conical shape, and the base portion includes a second end portion opening at a second end portion of the base portion into which the injection needle is inserted, the second end portion opening being formed at an angle of inclination which is substantially equal to an angle of inclination of an outer surface of the coupling portion.

3. The syringe receptacle of claim 2, wherein the base portion includes, on an inner peripheral surface thereof, a projection portion which is projectingly formed along a direction of inclination of the inner peripheral surface, the projection portion being capable of interfering, in a circumferential direction, with a projection which is formed on the outer surface of the coupling portion of the injection needle and has an angle of inclination which is equal to the angle of inclination of the second end portion opening.

4. A syringe receptacle comprising:

a base portion defining a communication hole, the base portion including a first end configured to mate with a syringe and a second end opposite to the first end;

a container airtightly mounted to the base portion between the first end and the second end of the base portion;

a stationary portion seated within the base portion at the second end, the stationary portion having a cylindrical shape and a closed end arranged proximate to the second end of the base portion;

first openings defined by the base portion and second openings defined by the stationary portion, the first openings are aligned with the second openings, the first and second openings permit fluid communication between the communication hole and the container when the first and second openings are open;

a first valve arranged within the communication hole such that the first and second openings are between the first valve and the second end of the base portion, the first valve defining a space within the communication hole between the first valve and the closed end of the stationary insert, the first valve is a stopper configured to close the communication hole and the space between the first valve and the closed end of the stationary portion, the first valve is formed of a resin material that is pierceable by the injection needle; and a second valve portion having a tubular shape and extending around an outer surface of the base portion opposite to the first openings and the second openings, the second valve portion is elastically deformable from a closed position to an open position when pressure in the space is greater than pressure in the container, in the closed position the second valve portion is against the first openings to prevent fluid within the space from flowing through the first and second openings into the container, in the open position the second valve is elastically deformed outward from the first openings to permit fluid within the space to flow through the first and second openings into the container.

* * * * *